United States Patent
Radl et al.

(10) Patent No.: US 10,813,648 B2
(45) Date of Patent: Oct. 27, 2020

(54) SYSTEMS AND METHODS FOR EFFECTING THE TOTAL AND PARTIAL OCCLUSION OF THE AORTA OF A LIVING BEING

(71) Applicant: Boehringer Technologies, LP, Phoenixville, PA (US)

(72) Inventors: Christopher L. Radl, Malvern, PA (US); Reed Vennel, Phoenixville, PA (US); Steven C. Moulden, West Chester, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 199 days.

(21) Appl. No.: 16/149,864

(22) Filed: Oct. 2, 2018

(65) Prior Publication Data
US 2019/0105057 A1    Apr. 11, 2019

Related U.S. Application Data

(60) Provisional application No. 62/588,621, filed on Nov. 20, 2017, provisional application No. 62/568,954, filed on Oct. 6, 2017.

(51) Int. Cl.
*A61B 17/12* (2006.01)
*A61B 17/00* (2006.01)
(Continued)

(52) U.S. Cl.
CPC .. *A61B 17/12136* (2013.01); *A61B 17/12031* (2013.01); *A61B 17/12036* (2013.01);
(Continued)

(58) Field of Classification Search
CPC ............... A61F 2/013; A61B 17/12136; A61B 17/12022–12195; A61M 25/1018; A61M 25/10181

See application file for complete search history.

(56) References Cited

U.S. PATENT DOCUMENTS 4,600,015 A * 7/1986 Evans .................... A61B 5/037
                                                          600/593
6,241,706 B1   6/2001 Leschinsky et al.
(Continued)

FOREIGN PATENT DOCUMENTS

WO    2016149653 A2   9/2016
WO    2017123655 A1   7/2017

OTHER PUBLICATIONS

International Search Report for PCT/US2018/054094 dated Jan. 28, 2019.

*Primary Examiner* — Wade Miles
(74) *Attorney, Agent, or Firm* — Caesar Rivise, PC

(57) ABSTRACT

Disclosed are systems and method for effecting the total and partial occlusion of a blood vessel, e.g., the aorta. The systems include a balloon catheter, a reservoir for an inflation fluid, a switch, and a pressure regulator/accumulator. The systems are configured to operate in a first mode and a second mode as established by the switch. During the first mode the balloon is fully inflated by the inflation fluid to completely occlude the blood vessel. During the second mode the balloon is partially inflated so that blood can flow past the balloon in the blood vessel. The pressure regulator/accumulator includes a chamber for receipt of the inflation fluid during the second mode to automatically regulate the pressure within the balloon to a desired operating pressure. The system is configured to operate in a third mode to prime the pressure regulator/accumulator to establish a desired operating pressure in the second mode.

10 Claims, 12 Drawing Sheets

(51) Int. Cl.
  *A61M 25/10*  (2013.01)
  *A61B 90/00*  (2016.01)

(52) U.S. Cl.
  CPC .............. *A61B 17/12109* (2013.01); *A61B 2017/00017* (2013.01); *A61B 2017/00022* (2013.01); *A61B 2017/1205* (2013.01); *A61B 2090/065* (2016.02); *A61M 25/10184* (2013.11)

(56) References Cited

U.S. PATENT DOCUMENTS

| | | |
|---|---|---|
| 8,177,704 B1 | 5/2012 | Mohl et al. |
| 2007/0060881 A1 | 3/2007 | Bonnette et al. |
| 2012/0302996 A1 | 11/2012 | Barash et al. |
| 2013/0102926 A1 | 4/2013 | Eliason et al. |
| 2014/0336690 A1* | 11/2014 | Zhadkevich ..... A61B 17/12136 606/194 |
| 2015/0327836 A1 | 11/2015 | Stone et al. |
| 2016/0000446 A1 | 1/2016 | Eliason et al. |
| 2016/0206798 A1 | 7/2016 | Williams et al. |
| 2017/0049457 A1 | 2/2017 | Hays et al. |
| 2017/0049946 A1* | 2/2017 | Kapur ................. A61M 1/125 |

\* cited by examiner

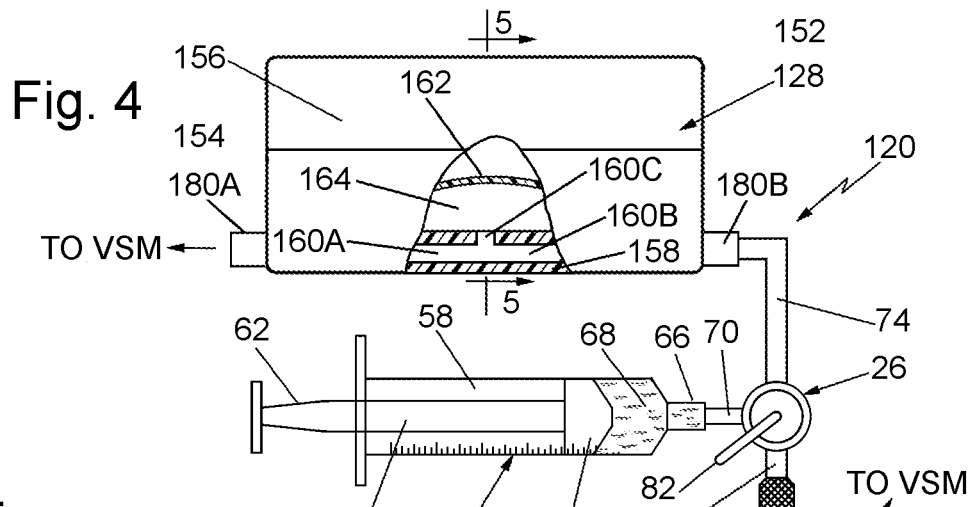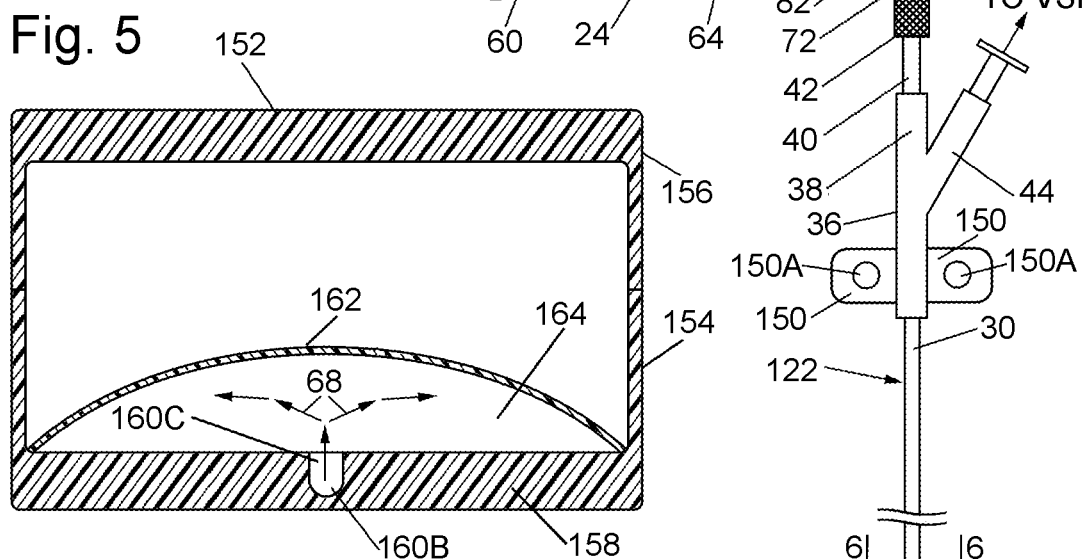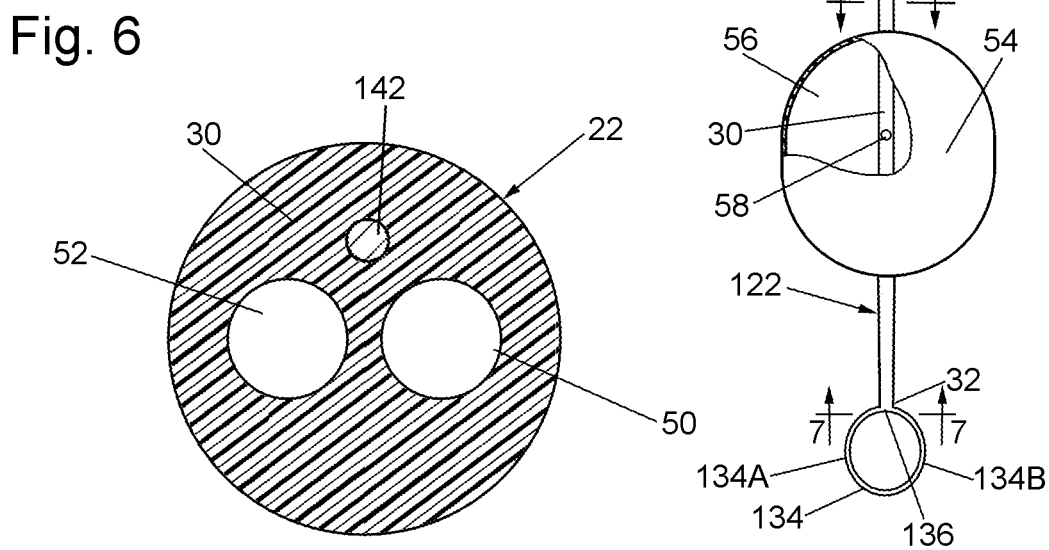

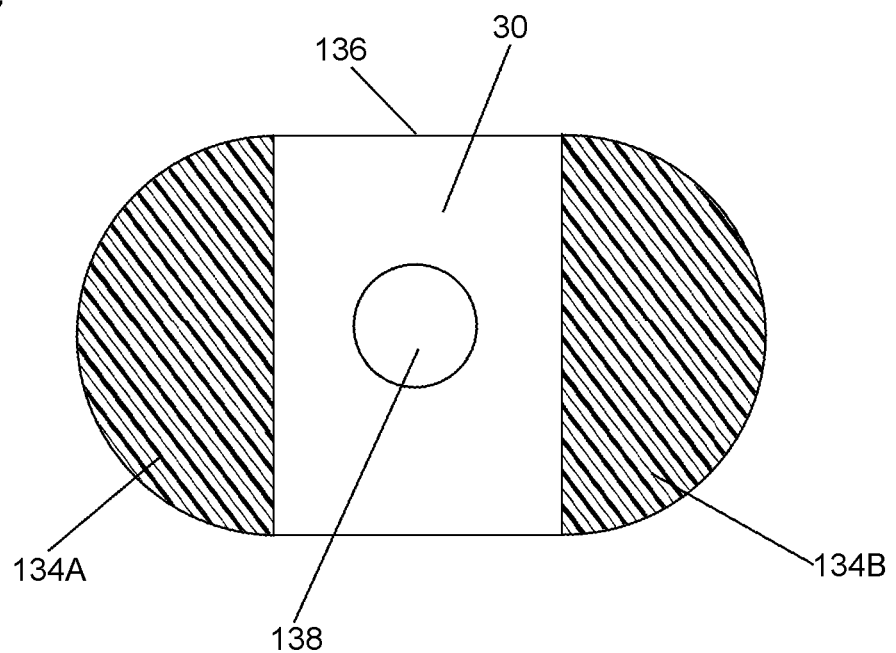

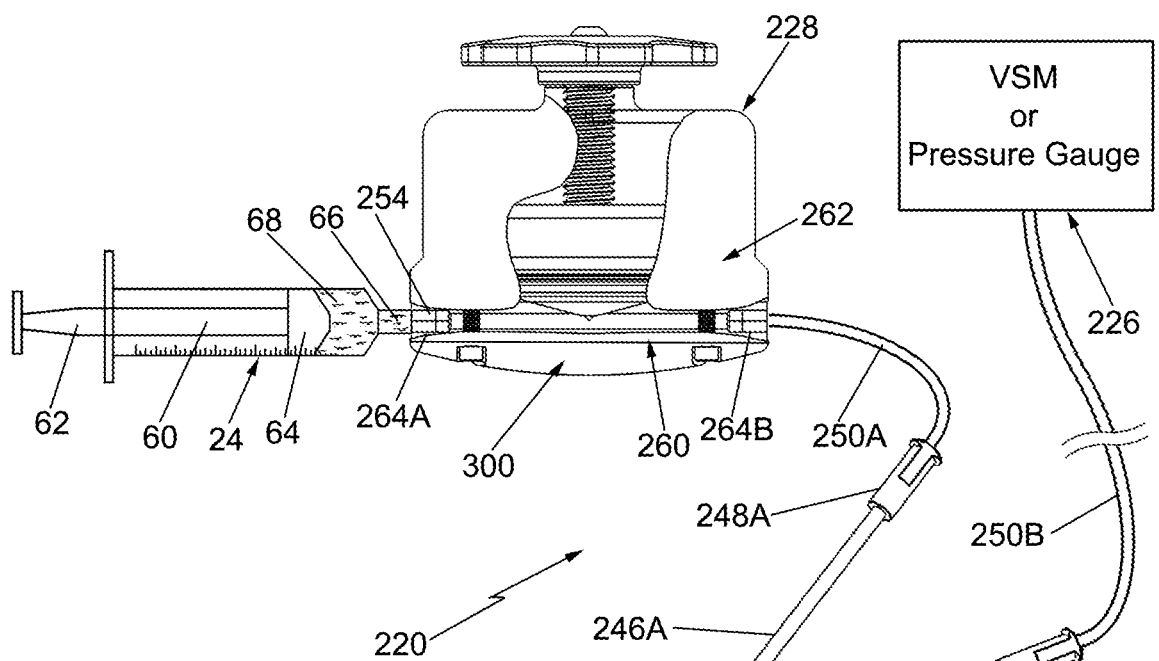
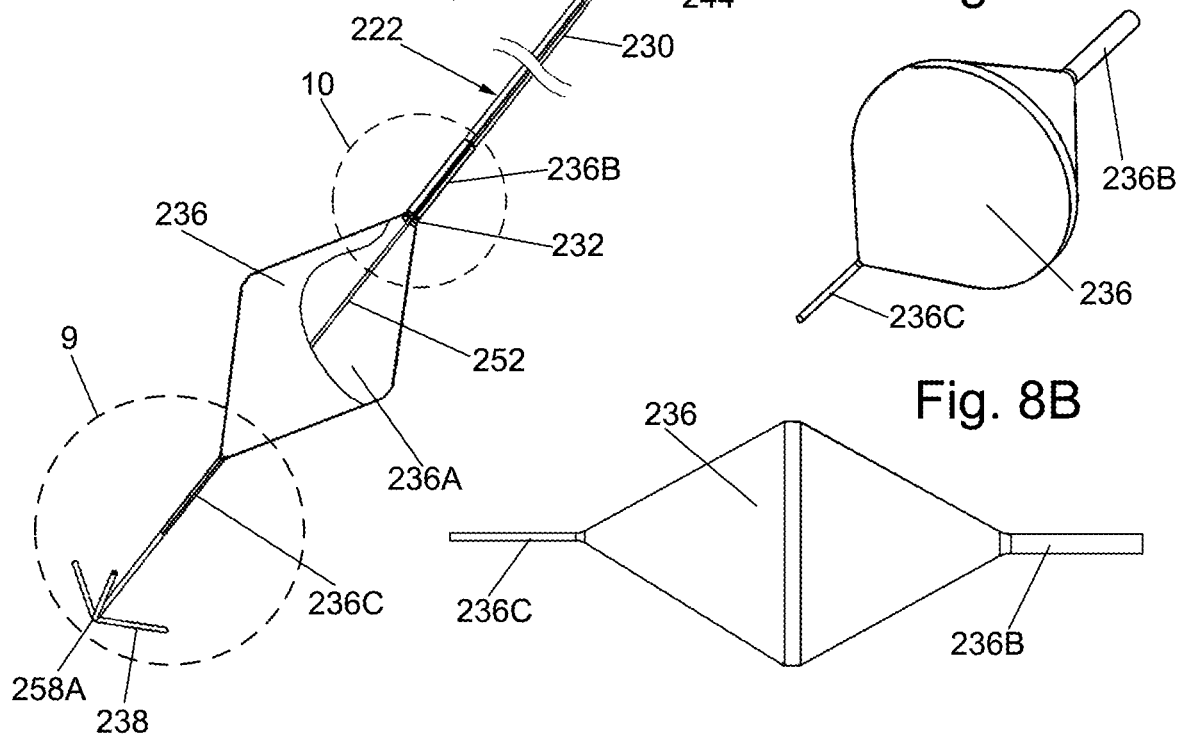

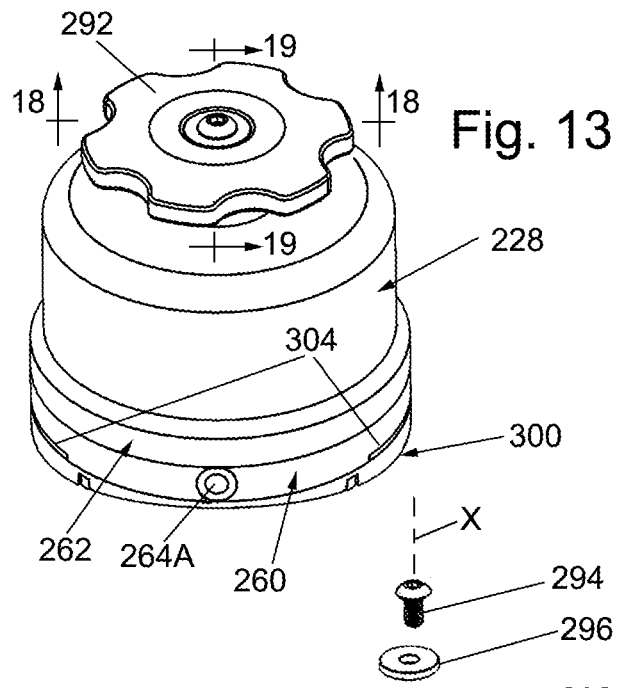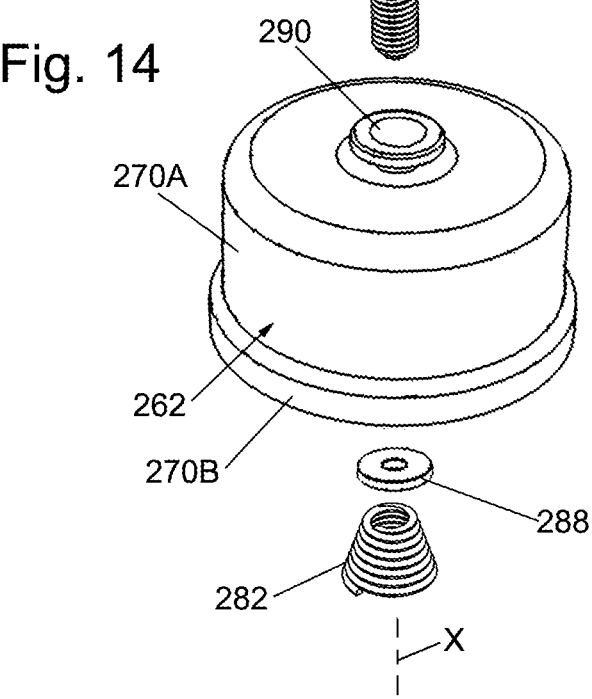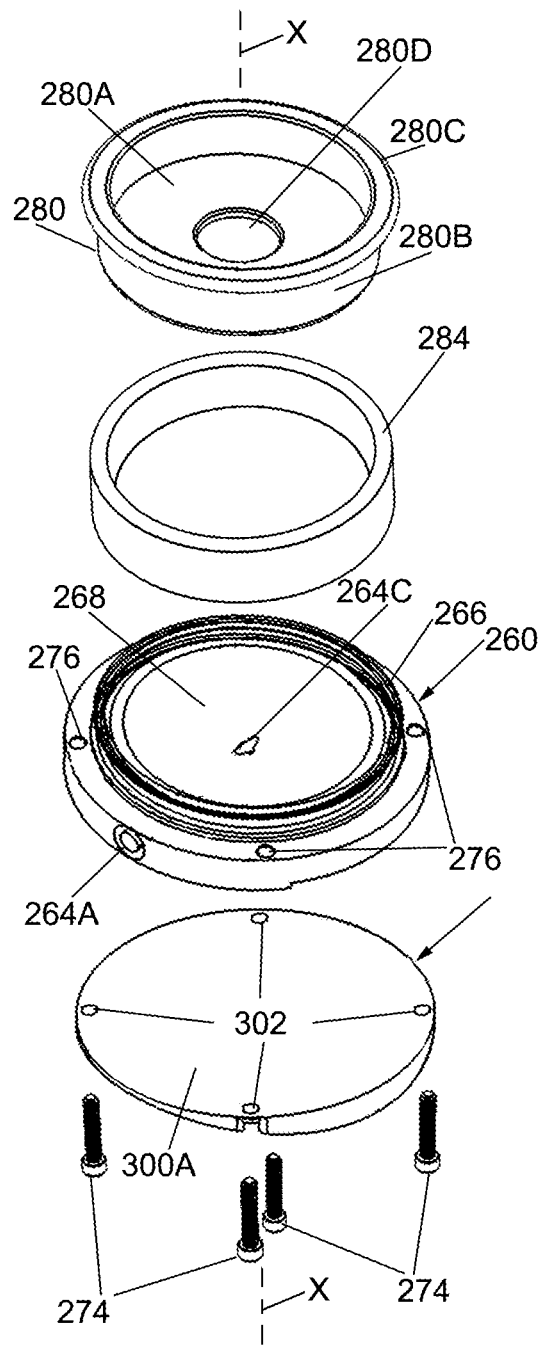

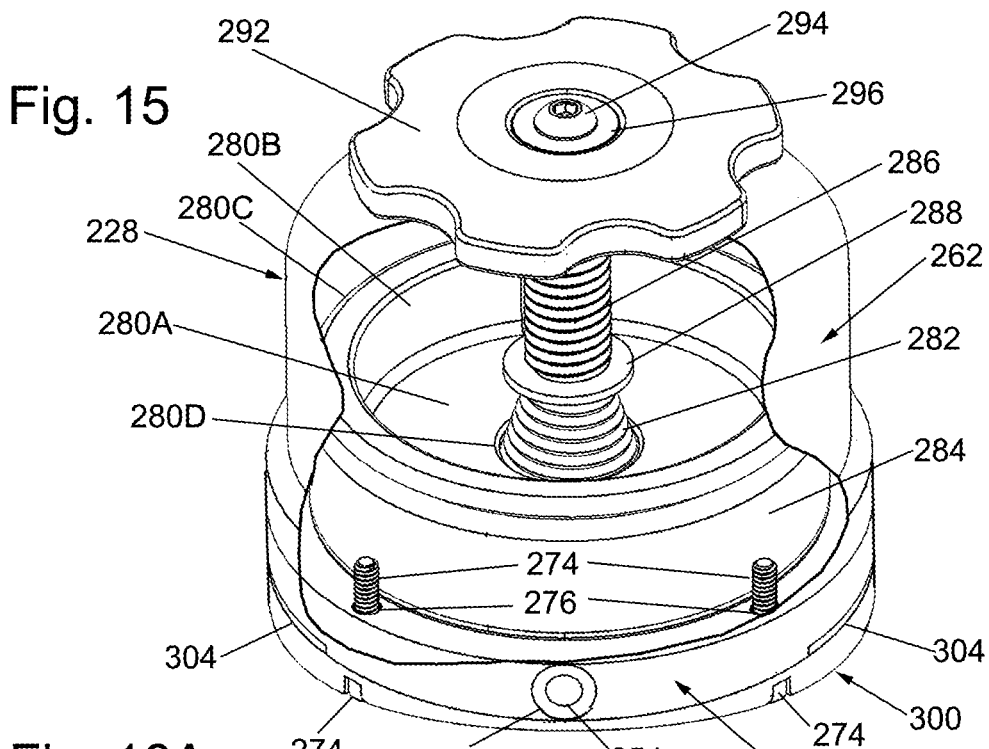
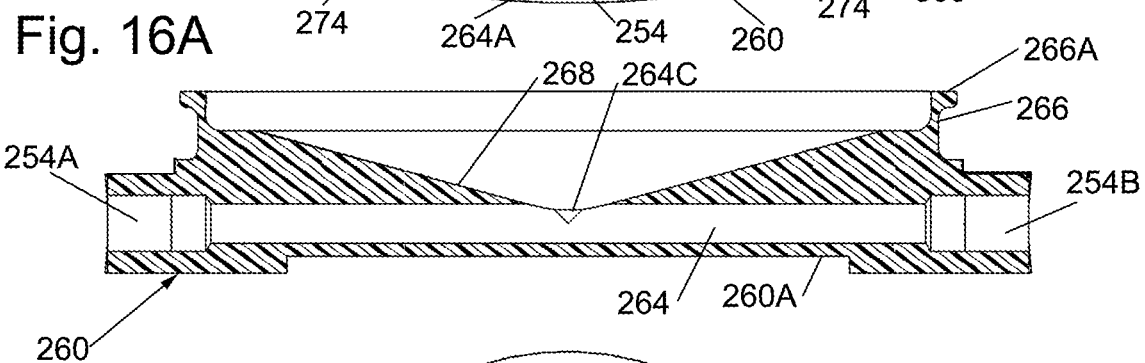
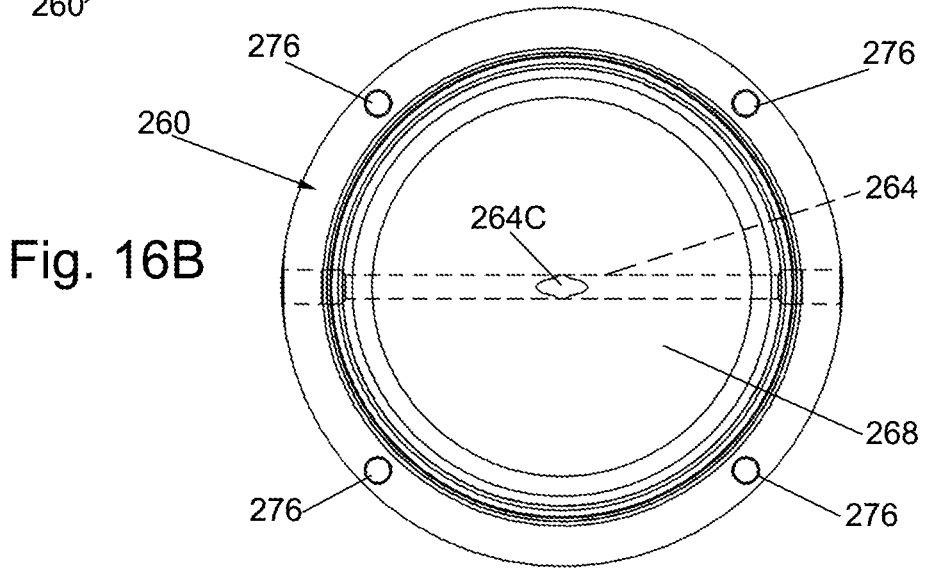

SYSTEMS AND METHODS FOR EFFECTING THE TOTAL AND PARTIAL OCCLUSION OF THE AORTA OF A LIVING BEING

CROSS-REFERENCE TO RELATED APPLICATIONS

This utility application claims the benefit under 35 U.S.C. § 119(e) of Provisional Application Ser. No. 62/568,954 filed on Oct. 6, 2017, entitled Device for Effecting the Total and Partial Occlusion of the Aorta of a Living Being and Method for Effecting the Total and Partial Occlusion of the Aorta of a Living Being, and Provisional Application Ser. No. 62/588,621, filed on Nov. 20, 2017, entitled Devices and Methods for Effecting the Total and Partial Occlusion of the Aorta of a Living Being. The entire disclosures of these provisional applications are incorporated by reference herein.

FIELD OF THE INVENTION

This invention relates generally to endovascular medical systems and methods of use and more particularly to systems and methods for achieving complete and partial resuscitative endovascular balloon occlusion of a blood vessel in the body of a living being.

BACKGROUND OF THE INVENTION

Resuscitative Endovascular Balloon Occlusion of the Aorta (commonly referred to as "REBOA") entails the placement of an endovascular balloon in the aorta to control hemorrhage and to augment afterload in traumatic arrest and hemorrhagic shock states. In particular, REBOA is commonly used in emergency departments to cut off blood flow to incompressible abdominal wounds. By cutting off blood flow to the injury site, the superior portion of the body (and most importantly, the brain) continues to receive perfusion, while blood loss is minimized. Because the brain is more sensitive to ischemia, this extends the operating window for surgeons to correct the damage before the patient dies. However, by completely occluding the descending aorta, the lower trunk and legs are starved of blood. This limits the operating window, as after approximately 30-60 minutes, the lower limbs and abdominal organs will become necrotic, requiring amputation or other extreme interventions.

Heretofore, REBOA procedures have been accomplished by use of a balloon catheter which is inflated by sterile fluid, e.g., saline, introduced into the catheter from a syringe to fully occlude the aorta. The patent literature includes various catheters which can be used to accomplish a REBOA procedure by occluding the aorta. Examples of such prior art is found in US2013/0102926 (Eliason et al.), US2015/0327836 (Stone et al.), US2016/0206798 (Williams et al.), US2017/0049457 (Hays et al.), WO2017/123655 (Keller et al.), and WO2016/149653 (Franklin et al.). In fact, the Franklin et al. reference discloses a device that is configured to selectively effect a partial occlusion of the aorta in addition to a complete aortic occlusion, whereupon blood can flow past the device during partial occlusion.

While the aforementioned prior art catheters and methods of use appear generally suitable for their intended purposes, they nevertheless leave something to be desired from one or more of the standpoints of effectiveness, ease of use, etc. Thus, a need exists for an endovascular occlusion system and method of use which overcomes the disadvantages of the prior art. The subject invention achieves that end by providing a balloon catheter system and method of use which enables full occlusion of a blood vessel, e.g., the aorta, when desired and thereafter partial occlusion of that vessel to permit carefully controlled amounts of blood to bypass the balloon, thereby maintaining brain perfusion, while extending the time to necrosis of the inferior portion of the body and limiting the risk of vascular injury from over-pressurization above the occlusion site. By so doing the subject invention can serve to increase the amount of time allowed for patient transport and surgical correction of the injury. Once the surgical correction is complete, the same system can allow gradual reperfusion below the occlusion site, thereby limiting reperfusion injury, and allowing transient reduced blood pressures to facilitate clotting.

BRIEF SUMMARY OF THE INVENTION

One aspect of this invention is a system for effecting the total and partial occlusion of a blood vessel of a living being. The vessel includes blood therein. The system comprises a catheter, a fluid reservoir, a balloon and a pressure regulator. The catheter has a distal end portion and at least one lumen extending through at least a portion of the catheter. The fluid reservoir is configured to be selectively coupled to the at least one lumen to introduce a metered volume of a sterile liquid into the at least one lumen when the system is in a first mode of operation. The balloon is located adjacent the distal end portion of the catheter. The balloon has a hollow interior coupled to the at least one lumen for selective receipt of the sterile liquid from the fluid reservoir to result in the full inflation of the balloon when the system is in the first mode of operation, thereby completely occluding the vessel to preclude blood from flowing past the balloon when the system is in the first mode of operation. The pressure regulator is configured when the system is in a second mode of operation to be coupled to the interior of the balloon via the at least one lumen to receive a portion of the sterile liquid from the balloon, whereupon the balloon is partially inflated to enable some blood in the vessel to flow past the balloon. The pressure regulator automatically regulates the pressure within the partially inflated balloon to a desired pressure when the system is in the second mode of operation.

In accordance with one preferred aspect of the system of this invention the system is configurable so that the desired pressure is adjustable.

In accordance with another preferred aspect of the system of this invention the pressure regulator comprises an expandable and collapsible chamber in which the sterile liquid is disposed. The expandable and collapsible chamber is configured to receive a predetermined volume of the sterile liquid introduced therein to result in the application of a predetermined amount of bias force on the predetermined volume of the sterile liquid, whereupon the adjustable desired pressure is produced in the partially inflated balloon.

In accordance with another preferred aspect of the system of this invention the expandable and collapsible chamber comprises a resilient diaphragm.

In accordance with another preferred aspect of the system of this invention the pressure regulator comprises a housing and wherein the resilient diaphragm is located within the housing.

In accordance with another preferred aspect of the system of this invention the balloon is configured to apply pressure in the range of approximately 40-250 mm Hg to the blood in the vessel.

In accordance with another preferred aspect of the system of this invention the distal end portion of the catheter terminates in an atraumatic tip.

In accordance with another preferred aspect of the system of this invention the atraumatic tip comprises a collapsible loop.

In accordance with another preferred aspect of the system of this invention the catheter comprises another lumen extending from the atraumatic tip to a proximal end portion of the catheter. The proximal end portion of the catheter is configured to be located outside of the body of the living being. The distal end portion of the catheter includes a pressure sensing opening located distally of the balloon adjacent the atraumatic tip. The proximal portion of the catheter is configured to be coupled to a measuring instrument to provide an indication of the pressure within the blood vessel at the pressure sensing opening.

In accordance with another preferred aspect of the system of this invention the catheter includes a proximal portion configured to be located outside of the body of the being. The proximal portion is configured to be secured to the skin of the being.

In accordance with another aspect of the system of this invention the system additionally comprises a switch to change the system from the first mode of operation to the second mode of operation, and vice versa.

In accordance with another aspect of the system of this invention the fluid reservoir comprises a syringe, and wherein the switch comprises a three-way stop-cock coupling the syringe and the balloon together when the system is in the first mode of operation, and wherein the three-way stop cock couples the balloon to the pressure regulator when the system is in the second mode of operation.

In accordance with another aspect of the system of this invention the system is configured to be in a third mode of operation wherein the three-way stop cock couples the syringe to the pressure regulator so that they are in fluid communication with each other and isolated from the balloon.

In accordance with another preferred aspect of the system of this invention the system additionally comprises a shape memory wire extending at least along a portion of the catheter.

In accordance with another preferred aspect of the system of this invention the proximal portion of the catheter includes at least one tab for releasable securement to the skin of the being.

Another aspect of this invention is a catheter for a system for effecting the total and partial occlusion of a blood vessel of a living being, the vessel including blood therein, the system being configured for a first mode of operation and a second mode of operation. The first mode of operation occludes the blood vessel. The second mode of operation partially occludes the blood vessel. The catheter comprises a distal end portion, at least one lumen and a balloon. The at least one lumen extends through at least a portion of the catheter and is configured to be selectively coupled a fluid reservoir to have a metered volume of a sterile liquid introduced into it to cause the system to be in the first mode of operation. The balloon is located adjacent the distal end portion of the catheter. The balloon has a hollow interior coupled to the at least one lumen for selective receipt of the sterile liquid from the fluid reservoir to result in the full inflation of the balloon whereupon the system will be in the first mode of operation, thereby completely occluding the vessel to preclude blood from flowing past the balloon. The catheter is configured to be coupled to an accumulator when the system is in the second mode of operation whereupon the accumulator automatically receives a portion of the sterile liquid from the balloon to cause the balloon to be partially inflated to enable some blood in the vessel to flow past the balloon.

In accordance with one preferred aspect of the catheter of this invention the balloon is configured to apply pressure in the range of approximately 80-150 mm of Hg to the blood in the vessel.

In accordance with another preferred aspect of the catheter of this invention the at least one lumen comprises an inflation lumen and a pressure-monitoring lumen, and wherein the balloon includes a proximal end portion and a distal end portion. The hollow interior of the balloon is coupled to the inflation lumen at the distal end portion of the catheter. The pressure-monitoring lumen extends through the hollow interior of the balloon and exits the balloon at the distal end portion of the balloon. The pressure monitoring lumen has a distal free end including a pressure-sensing opening.

In accordance with another preferred aspect of the catheter of this invention the pressure-monitoring lumen includes a proximal end portion configured to be coupled to a measuring instrument to provide an indication of the pressure within the blood vessel at the pressure-sensing opening.

In accordance with another preferred aspect of the catheter of this invention the distal free end comprises an atraumatic tip having a plurality of fingers located adjacent the pressure-sensing opening, the fingers projecting outwardly.

Still another aspect of this invention is a method for effecting the total and partial occlusion of a blood vessel, e.g., the aorta, in the body of a living being. The blood vessel includes blood therein. The method comprises introducing a catheter into the blood vessel of the being. The catheter has a distal end portion and at least one lumen extending through at least a portion of the catheter and an inflatable balloon located adjacent the distal end portion and coupled to the at least one lumen. A sterile liquid is selectively introduced into the at least one lumen to fully inflate the balloon during a first mode of operation, whereupon the fully inflated balloon completely occludes the blood vessel to preclude blood from flowing past the balloon. A pressure regulator is selectively coupled to the balloon during a second mode of operation, whereupon the pressure regulator receives a portion of the sterile liquid from the balloon so that the balloon is partially inflated to enable some blood in the blood vessel to flow past the balloon. The pressure regulator automatically regulates the pressure within the balloon to a desired pressure during the second mode of operation.

In accordance with one preferred aspect of the method of this invention the method additionally comprises sensing the amount of pressure applied to the blood in the blood vessel by the balloon.

In accordance with another preferred aspect of the method of this invention the desired pressure is adjustable.

In accordance with another preferred aspect of the method of this invention the pressure regulator comprises an expandable and collapsible chamber in which the sterile liquid is disposed. The method additionally comprises introducing a predetermined volume of the sterile liquid into the expandable and collapsible chamber to result in the application of a predetermined amount of bias force on the predetermined volume of the sterile liquid, whereupon the adjustable desired pressure is produced in the partially inflated balloon.

In accordance with another preferred aspect of the method of this invention the method additionally comprises initially introducing the predetermined volume of the sterile liquid into the expandable and collapsible chamber to remove any air from within the expandable and collapsible chamber.

In accordance with another preferred aspect of the method of this invention the expandable and collapsible chamber includes a resilient diaphragm configured to apply the predetermined amount of a bias force upon the introduction of the predetermined volume of the sterile liquid into the expandable chamber.

In accordance with another preferred aspect of the method of this invention the distal portion of the catheter terminates in an atraumatic tip.

In accordance with another preferred aspect of the method of this invention the atraumatic tip comprises a collapsible loop, and wherein the method comprises collapsing the loop to enable the catheter to be readily inserted into the blood vessel of the living being.

In accordance with another preferred aspect of the method of this invention the body of the living being has an inferior portion and wherein the method additionally comprises re-perfusing the inferior portion of the being's body by radial infusion.

In accordance with another preferred aspect of the method of this invention the re-perfusing is accomplished while the balloon is partially inflated.

In accordance with another preferred aspect of the method of this invention the method additionally comprises selectively removing the sterile liquid from the balloon to thereby deflate the balloon, whereupon the catheter can be removed from the body of the living being.

In accordance with another preferred aspect of the method of this invention the blood vessel comprises the aorta.

DETAILED DESCRIPTION OF PREFERRED EMBODIMENTS OF THE INVENTION

FIG. 4 is a plan view, not to scale, partially in section, of another and more preferred exemplary system constructed in accordance with this invention for effecting the total and partial occlusion of a blood vessel, e.g., the aorta, of a living patient for various medical procedures, e.g., repair of an incompressible abdominal injury or wound;

FIG. 5 is an enlarged sectional view of a pressure regulator/accumulator forming a portion of the system of FIG. 4 taken along line 5-5 of FIG. 4;

FIG. 6 is a greatly enlarged sectional view of a three lumen catheter forming a portion of the system of FIG. 4 taken along line 6-6 of FIG. 4;

FIG. 7 is a greatly enlarged sectional of an atraumatic tip forming a portion of the system of FIG. 4 taken along line 7-7 of FIG. 4;

FIG. 8 is a plan view, not to scale, partially in section, of another and most preferred exemplary system constructed in accordance with this invention for effecting the total and partial occlusion of a blood vessel, e.g., the aorta, of a living patient for various medical procedures, e.g., repair of an incompressible abdominal injury or wound;

FIG. 8A is an enlarged isometric view of a balloon forming a portion of the system shown in FIG. 8;

FIG. 8B is an enlarged side elevation view of the balloon shown in FIG. 8A;

FIG. 13 is an isometric view of a pressure regulator/accumulator forming a portion of the system of FIG. 8;

FIG. 14 is an exploded isometric view of the components making up the pressure regulator/accumulator shown in FIG. 13;

FIG. 15 is an enlarged isometric view, partially broken away, of the a pressure regulator/accumulator shown in FIG. 13;

FIG. 16A is an enlarged vertical sectional view of one of the components, i.e., a base, of the pressure regulator/accumulator shown in FIG. 13;

FIG. 16B is a reduced top plan view of the base of the a pressure regulator/accumulator shown in FIG. 16A;

DETAILED DESCRIPTION OF THE PREFERRED EMBODIMENTS OF THE INVENTION

Figure 1:
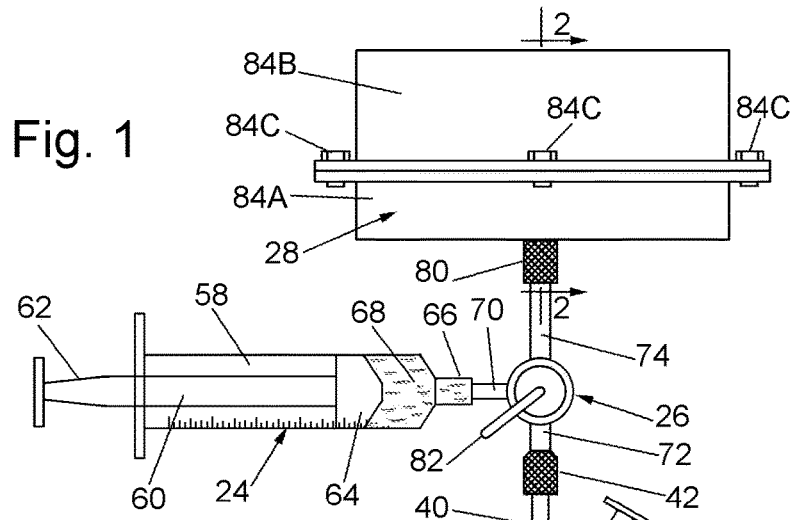
FIG. 1 is a plan view, not to scale, partially in section, of one exemplary system for effecting the total and partial occlusion of a blood vessel, e.g., the aorta, of a living patient for various medical procedures, e.g., repair of an incompressible abdominal injury or wound.

Referring now to the various figures of the drawing wherein like reference characters refer to like parts, there is shown in FIG. 1 an exemplary endovascular occlusion system 20 for effecting the total and partial occlusion of a blood vessel, e.g., the aorta, of a patient for an emergency medical procedure, e.g., repair of an injury or wound to a lower portion of the patient, e.g., an incompressible abdominal injury.

The system 20 basically comprises a multi-lumen balloon catheter 22, a syringe 24, a three-way fluid switch (e.g., stop cock) 26, and a pressure regulator 28. The system 20 is arranged to be used with a vascular access kit. The vascular access kit is not shown, but includes a conventional cannula, a conventional echogenic needle, and a conventional transverse ultrasound needle guide. The vascular access kit serves to allow rapid vascular access under ultrasound guidance to facilitate the placement of the catheter 22 into a desired position in the aorta. As will be described in detail later, the catheter 22 has at least one lumen to allow inflation of its balloon and at least one lumen to allow intravascular measurement of blood pressure distally of the free end of the catheter. The balloon is designed such that it can expand to the size needed to completely occlude the blood vessel with minimal internal pressure during a first mode of operation, which will be referred to as the "REBOA mode". The pressure regulator consists of an expandable/collapsible pressure chamber to allow the balloon to change volume to deflate somewhat to a partially inflated state or mode, which will be referred to as the "pREBOA mode". In the pREBOA mode the pressure regulator will maintain a constant pressure in the balloon. The pressure regulator may include pressure gauge (not shown) to indicate the pressure inside of the balloon.

Figure 3:
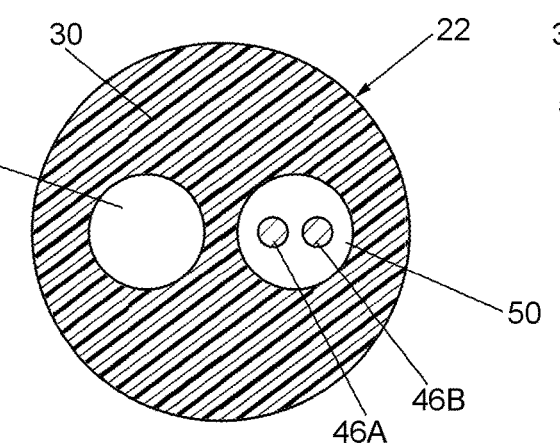
FIG. 3 is a greatly enlarged sectional view of a portion of a dual lumen catheter forming a portion of the system of FIG. 1 taken along line 3-3 of FIG. 1.

Turning now to FIGS. 1 and 3, the catheter 22 is of a conventional construction and includes an elongated flexible body 30 having a distal end 32 and a proximal end. The proximal end of the catheter body is connected to the distal end of a coupling 36 including a barrel section 38 through which a passageway (not shown) extends. The passageway is in fluid communication with a tubular conduit 40 having a proximal end in the form of a knurled connector 42. The coupling 36 also includes a side section 44. The side section is configured to be connected to a display device, e.g., a dial, a digital readout, a vital signs monitor, etc., (not shown) for displaying the pressure in the blood vessel immediately above the balloon when the system is in place. To that end, the side section 44 includes a passageway extending through it in which a pair of electrical conductors 46A and 46B (or a cable including at least two electrical conductors) extends, as will be described later. The electrical conductors are connected at their proximal end to the display device connected to the side section 44, and are connected at their distal end to a conventional pressure transducer or sensor 48, which is located at the distal end 32 of the catheter body 30.

The catheter body 30 includes at least two lumens extending through it. One lumen 50, shown in FIG. 3, serves to carry the electrical conductors 46A and 46B. The second lumen 52 serves to carry the sterile liquid for inflating and deflating the balloon of the catheter. The balloon is designated by the reference number 54, and as best seen in FIG. 1 is a thin walled flexible member having a hollow interior 56. The balloon is located closely adjacent the distal end of the catheter body 30. An opening or port 58 extends through the wall of the catheter body 30 and is in fluid communication with the distal end of the lumen 52. Thus, the interior of the balloon 54 will be in fluid communication with the lumen 52, via the port 58. The proximal end of the lumen 52 is in communication with the passageway extending through the barrel section 38 of the coupling 36 and is hence also in fluid communication with the conduit 40.

The means for inflating and deflating the balloon is preferably in the form of the syringe 24, but other means for providing a sterile inflation liquid into the balloon can be used. The syringe is of conventional construction having a hollow body 58 into which a plunger 60 extends. The plunger includes a cap 62 at the proximal end and an elastomeric disk 64 at the distal end. The distal end of the body 50 terminates at an outlet port 66. A sterile inflation liquid 68, e.g., saline, is disposed within the hollow interior of the syringe between the elastomeric disk 64 and the outlet port 66. The outlet port 66 is in fluid communication with a first port 70 of the three-way fluid switch 26. That switch is preferably in the form of a stop-cock, also having a second port 74 and a third port 72. The switch 26 can be of some other construction providing it has three ports, any two of which can be selectively coupled together so that the selected two ports are in fluid communication with each other.

The second port 74 of the stop-cock 26 is connected to and in fluid communication with a port 76 (FIG. 2) of the pressure regulator 28. The port 76 is in fluid communication with an expandable/contractible pressure chamber 78 (to be described later) in the pressure regulator. The connection between the second port 74 of the stop-cock 36 and the port 76 of the pressure regulator is achieved by means of a threaded knurled connector 80. The third port 72 of the stop-cock 26 is connected to the conduit 40 by the knurled connector 42. The stop-cock includes a rotatable lever 82 which is arranged to be rotated into one of three positions, namely a first position, a second position and a third position. In a first position, which serves as a full inflation position, the port 70 is in fluid communication with the port 72, while the port 74 is isolated from the ports 70 and 72. Thus, the inflation liquid 68 can be introduced or injected from the syringe 24 through the stop-cock and the conduit 40, through the passageway in the barrel section 38 of the coupling 36, from whence it passes into the lumen 52 of the catheter body 30, to exit the port 58 and thereby fully inflate the interior 56 of the balloon 54.

In the second position, which serves as the partial inflation position, the port 72 is in fluid communication with the port 74 so that there will be fluid communication between the interior 56 of the balloon and the pressure chamber 78 of the pressure regulator, while the port 70 is isolated from the ports 72 and 74. As will be described later, when the lever of the stop-cock is in the second position a portion of the inflation liquid 68 from the interior of the balloon will flow into the pressure chamber 78 to fill it, while partially deflating the balloon so that the balloon will be in a partially inflated state. Moreover, the pressure regulator will automatically establish the pressure within the partially inflated balloon to maintain it at a predetermined desired operating level, i.e., approximately 80 mm Hg., a level sufficient to ensure adequate perfusion of blood to the brain and heart, while allowing some blood to flow past the balloon towards the lower extremities of the patient's body to profuse tissue located thereat.

In the third position of the lever 82, which constitutes a position for "priming" the pressure regulator, the port 70 will be in fluid communication with the port 74, while the port 72 will be isolated from the port 70. Thus, as will be described later, a portion of the inflation liquid 68 can be introduced from the syringe into the expandable/contractible pressure chamber 78 when the lever 82 of the stop-cock 36 is in the third position to prime the pressure chamber 78.

Figure 2:
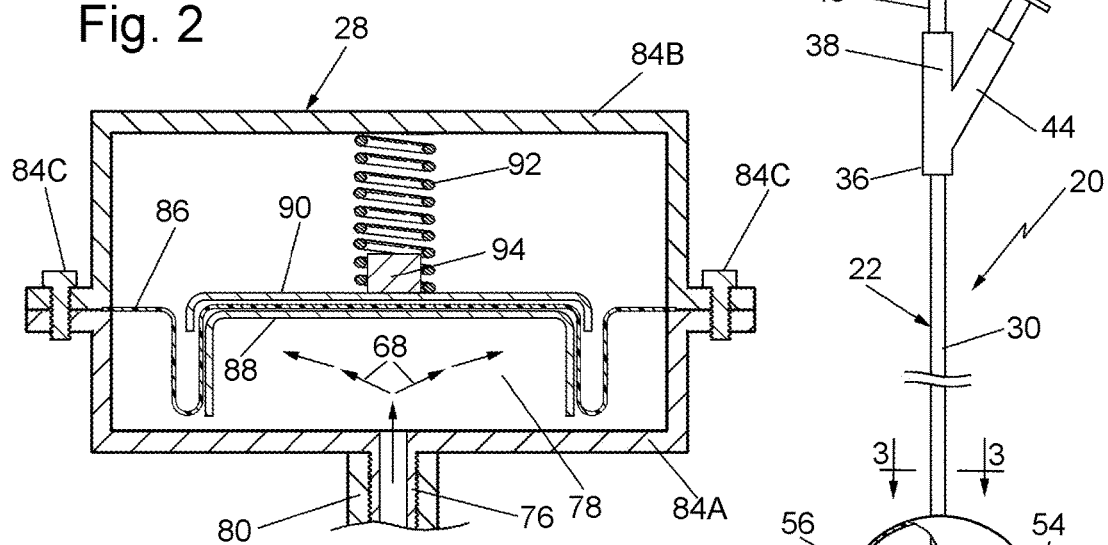
FIG. 2 is an enlarged sectional view of a pressure regulator/accumulator forming a portion of the system of FIG. 1 taken along line 2-2 of FIG. 1.

The details of the pressure regulator 28 will now be described with reference to FIG. 2. As can be seen the pressure regulator comprises a housing composed of two hollow flanged sections 84A and 84B which are secured together by threaded bolts 84C extending through the abutting flanges of those sections. The hollow interior of the section 84A forms a wall of the heretofore identified expandable/contractible pressure chamber 78. Another wall of that chamber and which completes the chamber is formed by a flexible diaphragm 86 whose periphery is fixedly secured between the flanges of the sections 84A and 84B. A relatively deep cup-shaped member 88, which forms a portion of a piston, is fixedly secured onto the inner surface of the diaphragm 86. A second portion of the piston is in the form of a shallow cup-shaped member 90 which is fixedly secured to the outer surface of the diaphragm 86. A helical compression spring 92 is interposed and under compression between the cup-shaped member 90 and the interior surface of the section 84B. The spring is configured to provide a bias force onto the piston to tend to push the piston and diaphragm towards the housing section 84A, thereby tending to contract the volume of the expandable/collapsible chamber 78. The amount of force applied by the spring 92 is such that the pressure on the inflation liquid 68 in that chamber will be at the desired operating level. In order to ensure that the spring remains in place and doesn't slip a centering plug 94 is fixedly secured to the outer surface of the cup shaped member 90 to fit within the hollow center of the helical spring 92.

The method of use of the system 20 will now be described with respect to the repair of an injury to a lower portion of a living patient, e.g., an incompressible abdominal injury. To that end, the femoral artery has to be accessed in order to insert the catheter 22 into the aorta. That action is accomplished in a conventional manner making use of the vascular access kit. In particular, a conventional ultrasound probe is used to locate the femoral artery, whereupon the probe is centered over the artery. A conventional needle guide is attached to the probe and the appropriate channel on the needle guide is selected based on the depth of the artery. A conventional needle is then placed in the appropriate channel of the needle guide so that the needle is guided into the femoral artery. The needle guide and probe are then removed and a conventional dilator is then used over the needle to enlarge the femoral puncture. A conventional cannula is then inserted into the femoral artery and threaded to a desired position within the aorta, whereupon the dilator and needle are then removed, leaving the cannula in place.

The catheter 22 is then threaded through the cannula so that its balloon 54 (which is uninflated at this time) is located at the desired site within the aorta. The pressure regulator 28, which is located outside the body of the patient, is then "primed" to remove any air within its pressure chamber 78 and to introduce the sterile inflation liquid 68 therein. That action is accomplished by switching the lever 82 of the three-way stop-cock 26 to the third position wherein the interior of the syringe 24 is in fluid communication with the interior of the pressure chamber 78. The plunger 60 of the syringe is then repeatedly extended and retracted (reciprocated) in a conventional manner to thereby prime the pressure regulator by introducing a desired amount of the sterile saline 68 into the pressure chamber while removing air from within that chamber. This priming action fills and pressurizes the pressure chamber, with the amount of pressurization of the chamber being adjustable and a function of the amount of sterile saline introduced into the chamber. The amount of pressurization of the pressure chamber should be the minimum sufficient to sustain superior blood circulation, e.g., approximately 80 mm Hg. To that end, the system 20 includes a pressure sensor (not shown) which may be located within the pressure regulator and coupled to the compression spring 92 to provide an indication of the pressure in the pressure chamber.

Once the pressure chamber has been evacuated of air, primed with some sterile saline 68 and pressurized, the system 20 is ready to be used in the REBOA mode to completely occlude the aorta by the full inflation of the balloon. To that end, the lever 82 of the three-way stop-cock is then moved to the first position wherein the interior of the syringe is in fluid communication with the lumen 52 in the catheter, but is isolated from the pressure chamber 78 in the pressure regulator 28. A desired amount (e.g., approximately 24 ml) of sterile saline is then introduced from the syringe through the lumen 52, whereupon the saline flows down the lumen and out through the port 58, thereby fully inflating the balloon to the state where it completely occludes the aorta so that the system is in the REBOA mode. At this time the pressure within the aorta above the balloon will be approximately 150 mm Hg. or higher. When in the REBOA mode the balloon will completely obstruct blood flow through the thoracic aorta inferiorly of the inflated balloon to promptly augment perfusion of the heart and brain with blood.

The surgeon or other medical care giver can then work on the patient to attempt to repair the injury or otherwise maintain the patient. However, the balloon can only be kept in its fully inflated (REBOA) state to completely occlude the descending aorta for a relatively short period of time, e.g., approximately one hour or less, to minimize the risk of the lower limbs and abdominal organs becoming necrotic. Thus, the system 20 is designed to enable the balloon to be switched into a partially inflated state or mode, i.e., the pREBOA mode, when desired. In the pREBOA mode some blood is enabled to flow past the balloon to perfuse tissues in the lower extremities of the patient.

As should be appreciated by those skilled in the art, the introduction of the sterile saline 68 into the pressure chamber during its priming expands the chamber against the bias of the spring, thereby establishing the operating pressure that the pressure regulator will maintain when the system is in the pREBOA mode. Preferably that operating pressure is approximately 80 mm Hg.

In order to place the system in the pREBOA mode all that is required is to move the lever 82 of the three-way stop-cock 36 to the second position, so that the port 72 is in fluid communication with the port 74. As such there will be fluid communication between the interior 56 of the balloon and the pressure chamber 78 of the pressure regulator, while the port 70 is isolated from the ports 72 and 74. In addition, the interior of the balloon and interior of the pressure chamber will be in fluid communication with each other, whereupon automatic superior pressure regulation ensues. In particular, once there is fluid communication between the interior of the balloon and the pressure chamber, the compression spring of the pressure regulator will automatically control the amount of pressure applied to the balloon to the desired operating pressure, e.g., approximately 80 mm Hg., to maintain brain perfusion, but enabling some blood to flow to the lower extremities. That action is accomplished by virtue of the fact that the higher pressure, e.g., 150 mm Hg. or above, that previously existed in the aorta by virtue of the complete occlusion of the aorta by the balloon, will force some of the sterile saline within the balloon through the port 58 and the communicating lumen 52 through the stop-cock 26 into the primed pressure chamber 78 as shown by the arrows in FIG.

2. The pressure chamber will thus expand against the bias provided by the spring 92 onto the piston and the associated diaphragm, whereupon the expanded pressure chamber will accept some of the sterile saline from the balloon. By so operating the pressure regulator 28 can be thought of as an accumulator and hence will be referred to as a pressure regulator/accumulator. Accordingly, the balloon will deflate somewhat, i.e., be partially inflated. For example, it may take on a wedge shape with small channels forming along the outer circumference of the balloon, thereby allowing small amounts of blood to bypass it, as a portion of the saline within the balloon is transferred to the pressure chamber of the pressure regulator/accumulator.

As mentioned earlier, the spring 92 is configured to provide a bias force which is sufficient to maintain brain perfusion, e.g., approximately 80 mm Hg. As also mentioned above, when the balloon is in its partially inflated pREBOA state some blood will be enabled to flow past the balloon to perfuse tissues of the lower extremities. The balloon 58 is configured so that it can be maintained in its pREBOA state to enable the surgeon or other medical personnel to attend to their surgical/interventional procedure on the patient to repair the wound, all the while monitoring the pressure in the aorta above the balloon by means of the pressure sensor 48.

It should be pointed out at this juncture, that when the balloon is in its partially inflated state, i.e., pREBOA mode, if for some reason it is desired to again fully occlude the aorta, i.e., place the system in its REBOA mode, all that is required is to again switch the lever 82 of the stop-cock to the first position wherein the stop-cock isolates the chamber 78 of the pressure regulator from the interior of the balloon, and reconnects the interior of the syringe to the interior of the balloon to establish fluid communication therebetween. Once that has been accomplished, the plunger 62 of the syringe 24 can be pressed to add additional sterile saline 68 into the interior of the balloon to fully inflate it again Once the surgical intervention, e.g., wound repair, has been accomplished in the pREBOA mode, the catheter 22 can be removed from the patient. That action is accomplished as follows. The blood pressure above the balloon is gradually increased by means of a radial IV or the like. The balloon will automatically allow some blood into inferior circulation to oppose the rising superior pressure. The higher the IV rate and superior pressure, the faster reperfusion will occur. Once inferior blood pressure has risen to match that of the superior pressure, the balloon will no longer oppose the blood pressure increase caused by infusion. Blood pressure will then rise systemically, and the balloon will deflate as the sterile saline transfers to the pressure chamber 78. Once this begins to occur, the lever of the three-way stop-cock is switched back to the first position, i.e., the REBOA mode, wherein the interior of the syringe is again in fluid communication with the interior of the balloon, but the pressure chamber of the pressure regulator is isolated from the interior of the balloon. At this time, the plunger of the syringe can be retracted to withdraw the sterite saline from the interior of the balloon through the port 58, the communicating lumen 52 and through the stop-cock 26 back into the syringe 24. When all of the sterile saline has been removed from the balloon, the balloon will be fully deflated. The catheter with its deflated balloon can then be withdrawn from the patient through the cannula. Once that has been accomplished the cannula can be removed and the femoral puncture repaired, if necessary.

In FIG. 4 there is shown a more preferred exemplary endovascular occlusion system 120 for effecting the total and partial occlusion of a blood vessel, e.g., the aorta, of a patient for an emergency medical procedure, e.g., repair of an injury or wound to a lower portion of the patient, e.g., an incompressible abdominal injury. The system 120 is similar to the system 20 in that it includes a multi-lumen balloon catheter 122, a syringe 24, a three-way fluid switch (e.g., stop cock) 26, and a pressure regulator/accumulator 128. The multi-lumen catheter 122 is similar in most respects to the catheter 22 described above except for some differences in its construction (to be described later). The syringe 24 and the three-way fluid switch (stop-cock) 26 are identical in construction to those components in the system 20. The pressure regulator/accumulator 128 provides a similar function to the pressure regulator/accumulator 28 described above, but is composed of different components, which will be also described in detail later. Thus, in the interest of brevity the common features of the systems 20 and 120 will be given the same reference characters and the details of their construction, arrangement and function will not be reiterated. Moreover, the operation of the system 120 will not be reiterated or described except for a description of the changes to the method that are occasioned by the differences in construction of the multi-lumen catheter 122 and the pressure regulator/accumulator 128.

Turning now to FIG. 4, the details of the construction and operation of the catheter 122 will be described. As can be seen the catheter 122 includes an elongated flexible body 30 having a distal end portion and a proximal end portion. The distal end portion of the catheter terminates in a collapsible loop 134 formed of the same material as the flexible body and serving as an atraumatic tip. The loop has a pair of side sections 134A and 134B, each of which is of arcuate, e.g., semi-circular, shape. The distal end of each of the side sections merge together smoothly to form the distal end or tip of the catheter which, being rounded is atraumatic. The proximal ends of the side sections 134A and 134B merge together at a junction 136 (FIGS. 4 and 7). The side sections 134A and 134B are inherently biased by the material of which they are formed so that in their natural state they form a loop. However, the sections 134A and 134B are collapsible so that they can be squeezed together to collapse them towards each other, thereby resulting in a small cross-section tip which can be readily inserted through the puncture in the patient's femoral artery to introduce the catheter 122 in place in the patient. Once the collapsed side sections of the atraumatic tip pass through the femoral puncture and into the femoral artery they will expand outward resulting in a somewhat circular enlarged tip which is resistant to snagging on any vascular side branch or injuring any portion of the patient's vasculature which the tip passes as the catheter is threaded into its operative position in the aorta.

As best seen in FIG. 7 an opening or port 138 is located at the junction 136 of the tip and thus is distal of the balloon 54. The port 138 will thus be in fluid communication with the interior of the aorta when the catheter is in place. The port 138 forms the distal end of the lumen 50, which in the case of the system 120 does not contain wires 46A and 46B since the system 120 does not make use of a pressure sensor 48 at the distal end of the catheter. Nevertheless, the system 120 is able to determine the pressure at the distal end of the catheter by means of a conventional vital signs monitor VSM which is arranged to be coupled to the side section 44 of the coupling 36. In particular, the passageway in the side section 44 will be in fluid communication with the vital signs monitor when the vital signs monitor VSM is coupled to the side section 44. The passageway in the side section is also in fluid communication with the lumen 50. Since the port 138 is in fluid communication with the lumen 50 and since that port 138 is open and in fluid communication with the blood in the aorta at the location of that port the vital signs monitor VSM can provide an indication of the blood pressure at the distal end of the catheter 122.

In order to facilitate the placement, e.g., threading, of the catheter 122 through the patient's vasculature to its operative location in the aorta the body of the catheter includes a shape-memory, e.g., Nitinol, wire 142 embedded in it as shown in FIG. 6 and extending the length of the catheter. The shape-memory wire 142 will tend to linearize the catheter and render it resistant to longitudinal collapse or deformation as it passes through the patient's vasculature from the femoral artery puncture (introduction) site.

In order to secure the catheter in the operative position in the aorta, the coupling 36 includes plural securement tabs 150 projecting outward. Each of those tabs may include an adhesive undersurface for adhesive securement to the skin of the patient adjacent the femoral artery puncture site. Alternatively, adhesive tape can be used to secure the tabs 150 to the skin of the patient. The tabs may include openings 150A to serve as a means for securing the tabs to the skin of the patient.

Attention is now directed to FIG. 5 where the details of the pressure regulator/accumulator 128 will now be discussed. The pressure regulator/accumulator 128 basically comprises a housing 152 formed of any suitable material. The housing is composed of two hollow sections 154 and 156 which are secured together by any suitable means (not shown). The section 156 includes a bottom 158 wall having two axially aligned, horizontally extending passageways 160A and 160B. A vertically oriented passageway 160C merges with the passageways 160A and 160B where they join together. The outer end of the passageway 160B is in the form of a conventional luer connector or lock 180B. The luer connector 180B is configured for connection to a mating luer connector (not shown) which forms the second port 74 of the three-way stop-cock 26. Alternatively, the luer connector 180B can be replaced by the knurled connector 80 and the end of the passageway 160B can be in the form of the externally threaded port 76, like that of the system 20. In such a case the second port 74 of the three-way stop-cock 26 will be constructed like that described of the system 20. The outer end of the passageway 160A is in the form of a luer connector 180A which is configured to be connected to another input of the vital signs monitor VSM or to a pressure gauge (not shown).

A resilient or elastic planar disk 162 is mounted within the lower section of the housing 152 above the bottom wall 158 to form a wall of an expandable/contractible pressure chamber 164. The pressure chamber 164 operates in a similar manner to the pressure chamber 78 of the system 20. The vertically oriented passageway 160C extends from the merger point of the passageways 160A and 160B to the space immediately below the disk 162. Accordingly, when the lever 82 of the three-way switch 26 is moved to the third position, i.e., the priming position, the sterile inflation saline from the syringe can be introduced through the port 74 and the communicating passageway 160B, from whence it flows through the passageway 160C into the expandable/contractible pressure chamber 164 during the priming operation of the system 120.

As will be appreciated by those skilled in the art the more sterile saline 68 from the syringe 24 that is introduced into the pressure chamber 164 will result in the greater stretching of the elastic disk 162 against the natural bias provided by the material making up the disk. Thus, the disk will bulge upward in a domed configuration like shown in FIGS. 4 and 5. As will also be appreciated by those skilled in the art, the amount of force that the disk 162 exerts on the saline 68 within the chamber will increase, as will the pressure on the saline. Since the passageway 160B is also coupled to the passageway 160C and hence to the interior of the chamber 164 the amount of pressure on the saline in the pressure chamber can be read/displayed by the vital signs monitor VSM (or the pressure gauge) that is coupled to the passageway 160A.

Operation of the system 120 is similar to that of the system 20 as described above, except for the introduction of the distal end of the system 120 into the femoral puncture. In this regard, as described above the two side sections 134A and 134B of the atraumatic tip are squeezed together to introduce the tip into the femoral puncture, whereupon those sections then expand outward. The rounded or looped distal end of the catheter can then be threaded through the femoral artery and other portions of the patient's vasculature until it is located at its desired location in the aorta of the patient. If the system 120 had not already been primed to establish the desired operating pressure such action can be accomplished by moving the lever 82 to the third or priming position thereby coupling the port 70 to the port 74, whereupon the repeated reciprocating of the syringe's plunger will introduce the sterile inflation saline 68 into the chamber 164, while removing any air therefrom. Once the chamber has been sufficiently primed to establish the desired operating pressure, e.g., 80 mm Hg, the lever can be moved to the first position for REBOA operation like that described above. Whenever pREBOA operation is desired, all that is necessary is to move the lever 82 of the switch 36 to the second position, whereupon saline from the interior of the balloon will flow through the passageways as previously described to enter into passageway 160B from whence it flows through passageway 160C into the pressure chamber 164. The resilient disk 162 will then stretch causing the chamber 164 to expand to accept saline from the balloon to maintain the operating pressure as established during the priming of the chamber in the same manner as described heretofore, whereupon the balloon will deflate somewhat to enable some blood to flow around it thereby perfusing downstream tissue.

Turning now to FIGS. 8-20 there is shown another and most preferred exemplary embodiment of a system 220 for effecting the total and partial occlusion of a blood vessel of a living being. As will be described in detail later, the system 220 includes a pressure regulator/accumulator 228 which is similar in operation to the pressure regulators/accumulators 28 and 128. However, the system 220 does not include the three-way stop cock 26 or any similar component. Nevertheless, the system 220 is configured to operate in the same three modes of operation as the systems 20 and 120 described above, namely, the first or REBOA mode, the second or pREBOA mode, and the third or "priming" mode. Accordingly, the system 220 is simpler and easier to use than the systems 20 and 120, while eliminating the chance that the stop cock could be accidentally moved to an undesired position during use of the system.

The system 220 basically comprises a multi-lumen balloon catheter 222, a syringe 24, and a pressure regulator/accumulator 228. The catheter 222 includes an elongated flexible body 230 having a distal end 232 and a proximal end 234. An inflatable balloon 236 is located at the distal end of the body 230. An atraumatic tip 238 is located distally of the balloon 236. The body 230 is preferably a flexible extrusion of polyurethane and includes two lumens, 240 and 242 (FIGS. 11 and 12) extending longitudinally therethrough from the proximal end to the distal end. The lumen 240 serves to carry the sterile liquid (e.g., saline) 68 for inflating and deflating the balloon 236, while the lumen 242 serves to monitor the pressure at the location of pressure monitoring port (to be described later) at the distal end of the atraumatic tip 238.

The lumen 240 is semilunar or crescent shaped and surrounds the lumen 242. This arrangement maximizes the available cross-sectional area for inflation/deflation, speeding the rate at which fluid 68 can flow into or out of the balloon. As will be appreciated by those skilled in the art faster flow means that the REBOA mode can be achieved more rapidly in patients where every second may be critical to survival, and also means that the pressure regulator/accumulator 228 will be able to respond to changes in blood pressure more rapidly during partial pREBOA operation.

The proximal end of the catheter body 230 terminates in an overmolded bifurcation piece 244, which is preferably formed of rigid plastic e.g., polyurethane. The bifurcation piece includes two arms 244A and 244B and a main or common section 244C. The arm 244A includes a lumen extending through it and through the main section 244C which is in fluid communication with the inflation/deflation lumen 240 of the catheter body 230. The arm 244A is connected to a single lumen extension tube 246A such that the lumen in the arm 244A is in fluid communication with the lumen in the single lumen extension tube 246A. The proximal end of the single lumen extension tube 246A terminates in a female luer lock 248A which is in communication with the lumen in that arm. The female luer lock 248A is configured to receive a male luer lock (not shown) that is overmolded on the distal end of a flexible, single lumen tube 250A. The tube 250A includes at its proximal end an overmolded male luer lock (not shown) configured to be received in a port 264B of the pressure regulator accumulator 228 to effect the inflation/deflation of the balloon 236. The arm 244B is connected to a single lumen extension tube 246B such that the lumen in the arm 244B is in fluid communication with the lumen in the single lumen extension tube 246B. The proximal end of the single lumen extension tube 246B terminates in a female luer lock or connector 248B which is in communication with the lumen in the arm 246B. The luer lock 248B is configured to receive a male luer lock (not shown) that is overmolded on the distal end of a flexible, single lumen tube 250B. The tube 250B is connected to a vital signs monitor VSM 226 or to a pressure gauge for displaying the pressure in the blood vessel at the atraumatic tip when the system is in place.

The foregoing arrangement of the bifurcation piece 244 and its connected tubes allows the luer locks to be a sufficient distance, e.g., 3", away from the bifurcation piece 244. This reduces the likelihood of the two fittings (or attachments) obstructing one another. Additionally, the extension tubes are significantly more flexible than the main extrusion, allowing easier connection to the vital signs monitor 226.

Figure 9:
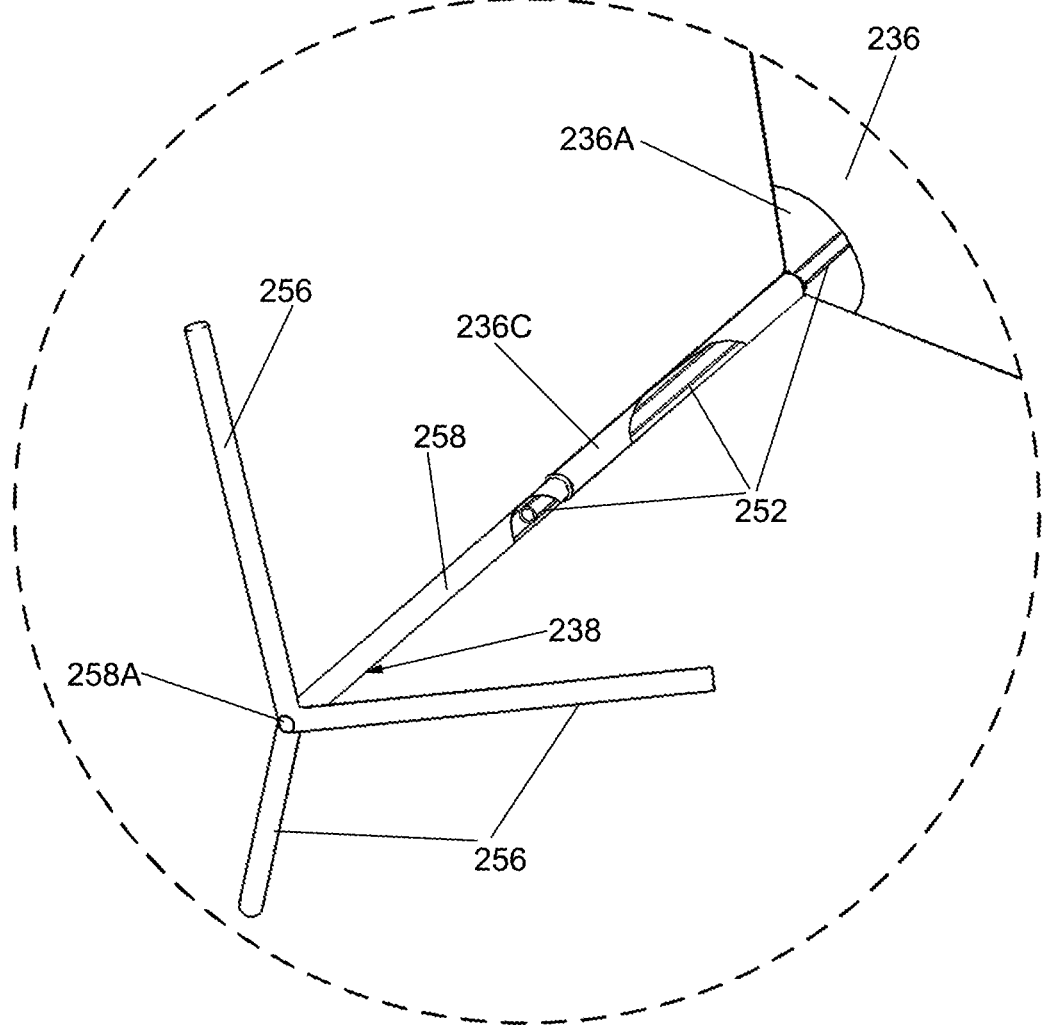
FIG. 9 is a greatly enlarged isometric view, partially in section, of an atraumatic tip and distal portion of an inflatable balloon forming a portion of the system of FIG. 8 which are shown within the broken circle designated by the reference number 9 in FIG. 8.
Figure 10:
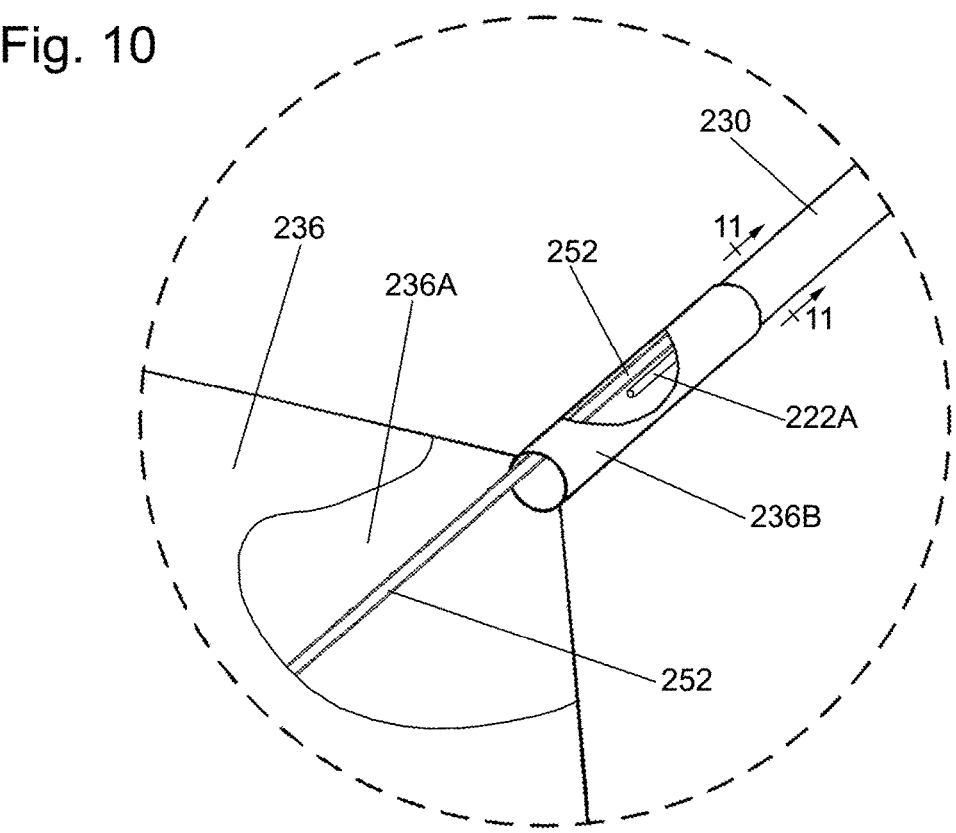
FIG. 10 is a greatly enlarged isometric view, partially in section, of the proximal portion of the inflatable balloon and a distal portion of a dual lumen extrusion forming a portion of the system of FIG. 8 which are shown within the broken circle designated by the reference number 10 in FIG. 8.

As best seen in FIGS. 8A and 8B the balloon 236 is a thin walled flexible member formed of polyurethane having a hollow interior 236 (FIG. 8). The balloon is mounted on the distal end of the catheter body 230, with the interior 236A of the balloon in fluid communication with the inflation lumen 240. Unlike the balloon 54, the balloon 236 is of a generally diamond-like shape. This configuration reduces the bulk of the material forming the balloon when the balloon is folded or otherwise collapsed for insertion into the patient's vascular system, while still allowing the balloon to achieve a desired diameter, e.g., 32 mm, suitable for REBOA operation with minimal internal pressure and without requiring the balloon to stretch. The fact that the balloon walls do not stretch means that they will not exert pressure on the liquid in the interior of the balloon. This allows the balloon to function as a "slack diaphragm" such that the pressure inside the balloon will be representative of the desired intra-aortic pressure. This is important, because it would mean that (for example) if the balloon is inflated to 80 mm Hg, all of that pressure would be opposing the blood above the balloon, so any blood in excess of 80 mm Hg will be allowed to flow. If the balloon didn't function as a slack diaphragm, then a blood pressure lower than the 80 mm Hg inside the balloon would result in blood bypassing the balloon. As best seen in FIG. 10 the proximal end of the balloon is in the form of a tubular neck or collar 236B which is fixedly secured to the distal end of the catheter body 230 and with the lumen 240 of the catheter body in fluid communication with the lumen of the collar or neck 236B. Moreover, the lumen of the collar 236B is in fluid communication with the interior 236 of the balloon. As best seen in FIG. 9 the distal end of the balloon is in the form of a smaller diameter tubular neck or collar 236C which is fixedly secured to the proximal end of the atraumatic tip 238 as will be described shortly.

A small diameter bridge tube 252 having a proximal end is provided located within the distal end of the pressure monitoring lumen 242 of the catheter body 230. The bridge tube 252 is formed of Nitinol or some other shape memory material and serves to couple the pressure monitoring lumen 242 to a pressure monitoring port at the distal end of the atraumatic tip 238. To that end, the proximal portion of the bridge tube is located and in fluid communication with the distal end of the pressure monitoring lumen in the catheter body. The bridge tube extends through the collar 236B and into the interior 236A of the balloon from whence its distal end exits the distal collar 236C for connection to the atraumatic tip 238. It may also be desired to add radiopaque marker bands to the catheter either on the bridge tube, or near the edges of the bridge tube. This would allow fluoroscopic confirmation of the catheter placement, as the radiopaque marker bands would be readily visible upon imaging, e.g., X-ray.

Figure 11:
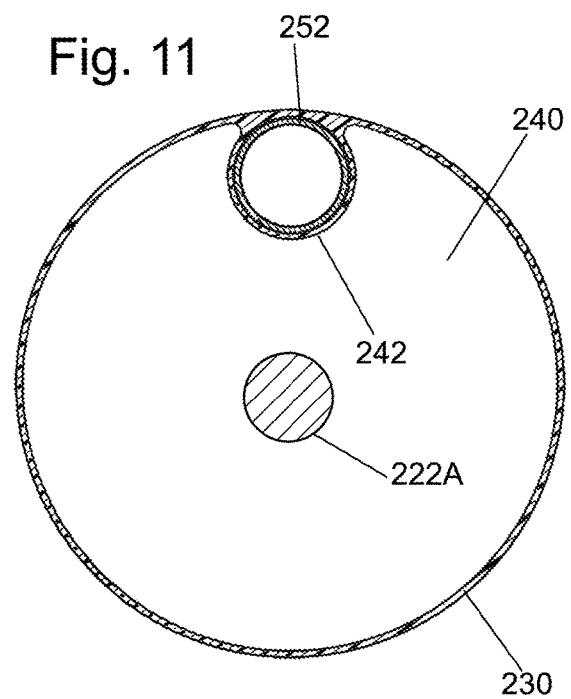
FIG. 11 is a greatly enlarged sectional view of the dual lumen extrusion and a tubular bridge member forming a portion of the system of FIG. 8 shown taken along line 11-11 of FIG. 10.
Figure 12:
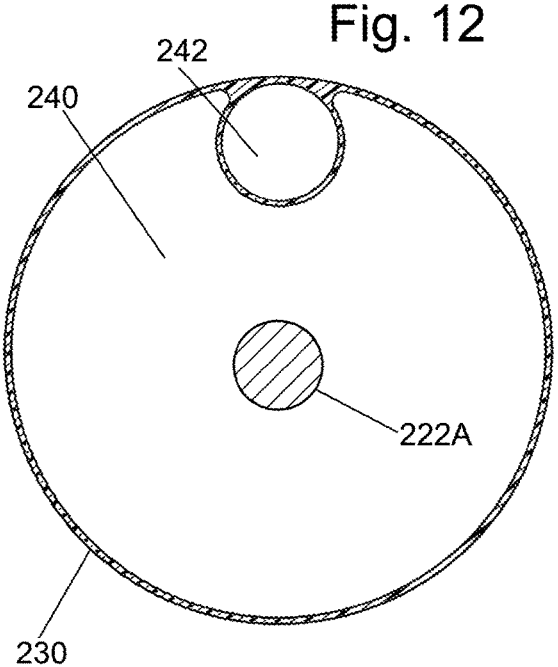
FIG. 12 is a greatly enlarged sectional view like that of FIG. 11, but showing the dual lumen extrusion without the tubular bridge member.
Figure 17:
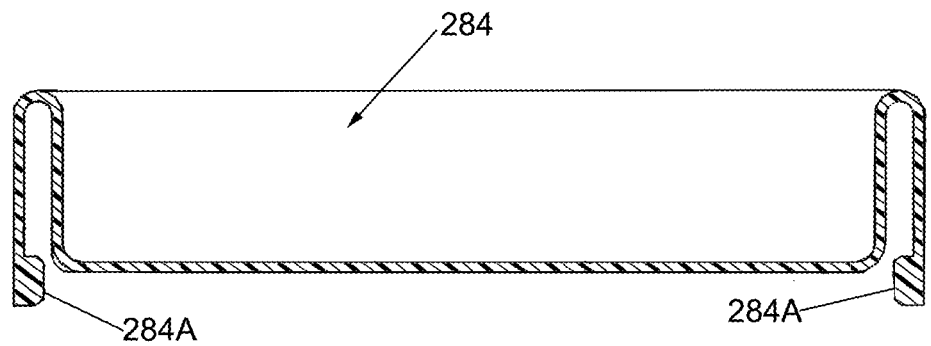
FIG. 17 is an enlarged vertical sectional view of one of the components, i.e., a resilient rolling diaphragm, forming a portion of the pressure regulator/accumulator shown in FIG. 13.

In order to facilitate the placement, e.g., threading, of the catheter 222 through the patient's vasculature to its operative location in the aorta the body of the catheter includes a shape-memory, e.g., Nitinol, wire 222A extending down the center of the catheter as shown in FIGS. 10-12 from the bifurcation piece 244 to a point within the neck or collar 236B of the balloon. The shape-memory wire 222A will tend to linearize the catheter and render it resistant to longitudinal collapse or deformation as it passes through the patient's vasculature from the femoral artery puncture (introduction) site.

The atraumatic tip 238 is best seen in FIG. 9 and basically comprises a central tubular shaft 258 whose proximal end is fixedly secured within the lumen of the collar 236C of the balloon. The distal end of the tubular shaft 258 is open to form the heretofore pressure monitoring port, now designated by the reference number 258A. The distal end of the bridge tube 252 is fixedly secured within the lumen in the tubular shaft 258 so that the pressure monitoring port 258A is in fluid communication with the lumen in the bridge tube and hence with the pressure monitoring lumen 242 of the catheter. Three linear elongated wings or projections 256 extend at an acute angle outwardly and proximally from the proximal end of the tubular shaft at the location of the pressure monitoring port 258A. Preferably, the atraumatic tip is formed as an integral unit of a softer plastic than the catheter body to reduce forces on tissues when it directly impacts them, and the three wings serve to help keep the catheter centered in the blood vessels during insertion. Moreover, by having three wings, the catheter is less likely to fold sideways to enter smaller blood vessels and is less likely to directly impact the vessel wall with the tip.

The inflation and deflation of the balloon is accomplished by the operation of the pressure regulator/accumulator 228 and in particular by the transference of the inflation/deflation liquid (e.g., saline) 68 from/to it. Turning now to FIGS. 13-20 the details of the pressure regulator/accumulator 228 will now be described. The pressure regulator/accumulator 228 includes a base 260 and a body 262 which together define an interior space including an expansion/contraction chamber for the inflation/deflation liquid 68. In accordance with one preferred aspect of this invention, the assembly of the base 260 and body 262 is configured to be mounted on the patient's thigh, the operating table, a rail on the bed during transport, or other stable location near to the patient's femoral access site so that the pressure regulator/accumulator will not clutter the surgical field. To that end the pressure regulator/accumulator 228 includes a strap mount 300 secured to the base 260. The details of the strap mount 300 will be described later.

The base 260 is best seen in FIGS. 13-16B and a solid disk-like member of circular profile (although it can be of any profile), which is an integral unit formed of any suitable rigid material, e.g., polycarbonate. The base includes a hollow conduit or passageway 264 extending diametrically through it and an annular wall 266 (FIG. 16A) projecting upward from its upper surface. The annular wall 266 includes an outwardly extending annular flange 266A. The portion of the upper surface of the base 260 which is bounded by the annular wall 266 is in the form of a conical cut-out or recess 268. The recess 268 has an ovoid shaped opening 264C (FIGS. 16A and 16B) at its nadir. That opening is in fluid communication with the conduit 264 at the midpoint of the conduit.

The conduit 264 serves as the means through which the inflation liquid 68 enters and exits the pressure regulator/accumulator 228. In particular, one end 264A of the conduit 264 forms a port for the introduction of the priming and REBOA producing liquid 68 into the pressure regulator/accumulator 228. The port 264A includes a needleless injection site, male luer lock 254 (FIG. 8). One particularly suitable needleless injection site, male luer lock is sold under the part number 80147 by Qosina of Ronkonkoma, N.Y. That male luer lock is swabbable. Other needless injection site male luer locks, whether swabbable or not, can be used in lieu of the exemplary one. The needleless injection site male luer lock 254 is configured for receipt of the outlet 66 of the syringe 24, whereupon when the outlet of the syringe is introduced into the luer lock, and the plunger 60 pushed to eject the inflation liquid 68 from the syringe, the luer lock 254 opens to enable the inflation liquid 68 to flow into the conduit 264. The opposite end of the conduit 264 serves as the outlet port 264B of the pressure regulator/accumulator through which the inflation liquid 68 is introduced into the catheter 222 to inflate the balloon in the REBOA mode. Moreover, the port 264B also serves as an inlet port from which a portion of the inflation liquid 68 in the balloon is transferred back into the pressure regulator/accumulator when the system is in its pREBOA mode of operation. The port 264B is in the form of a female luer lock configured for receipt of the male luer fitting on the proximal end of the single lumen tube 250A.

Figure 18:
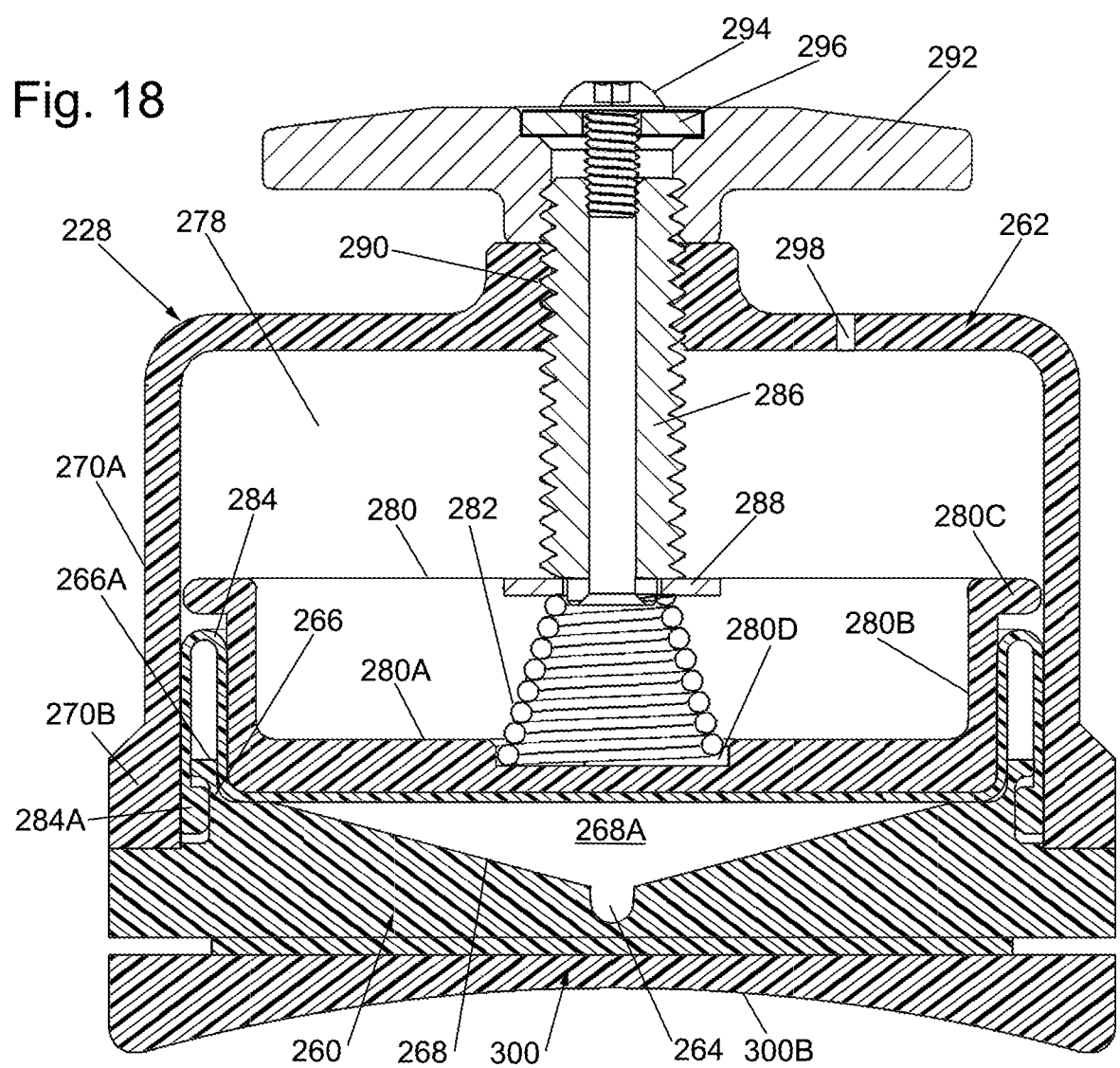
FIG. 18 is an enlarged vertical sectional taken along line 18-18 of FIG. 13.
Figure 19:
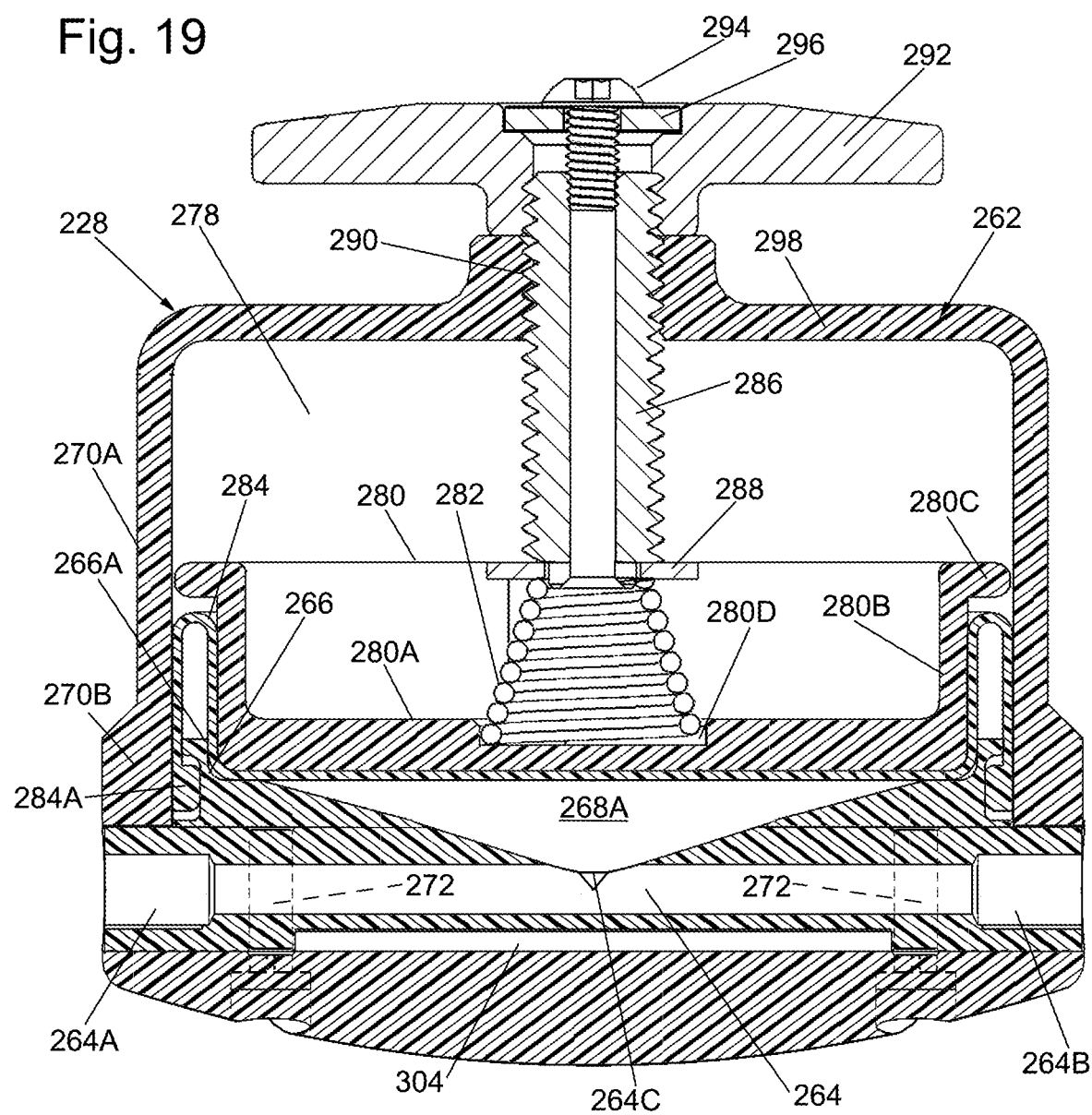
FIG. 19 is an enlarged vertical sectional view taken along line 19-19 of FIG. 13.
Figure 20:
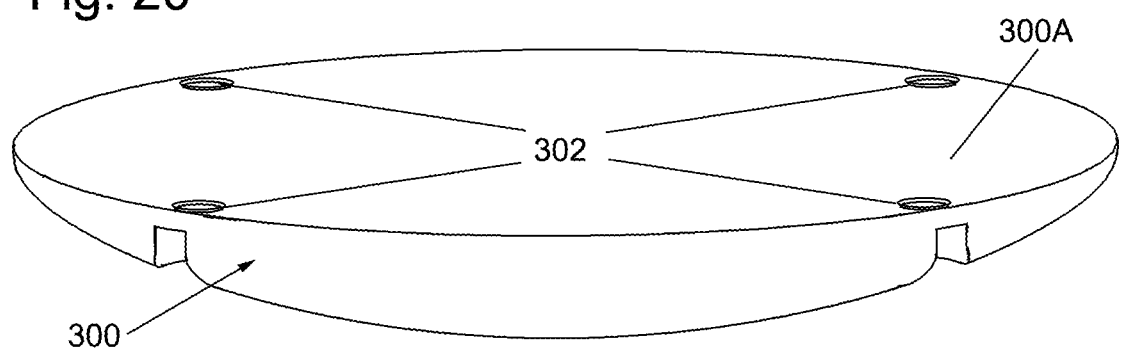
FIG. 20 is an isometric view of another of the components, i.e., a strap mount, forming a portion of the pressure regulator/accumulator shown in FIG. 13.

The body 262 is best seen in FIGS. 14, 18 and 19 and a cup shaped member that is formed of any suitable rigid material, e.g., polycarbonate. The body has a cylindrical side wall 270A terminating at its bottom in an annular flange 270B. The flange 270B is disposed on the upper surface of the portion of the base 260 lying just outside the annular flange 266. The annular flange 270B includes four internally threaded bores 272 (FIG. 19) for receipt of respective externally threaded fasteners, e.g., stainless steel socket head cap screws 274. Those screws extend through respective holes (to be described later) in the strap mount 300, and through aligned openings 276 in the base 260 to secure the body 262 to the base 262 and to the strap mount 300. With the body secured to the base an interior space 278 (FIGS. 18 and 19) is created between the conical recess and the inner surface of the body 262.

A piston 280 (FIGS. 14, 15, 18 and 19) formed of rigid material, e.g., nylon, is located within the interior space 278. The piston is a cup-shaped member having a circular bottom wall 280A from which peripheral side wall 280B projects upward. The upper edge of the side wall 280B is in the form of an outwardly extending annular flange 280C. The flange is configured for sliding engagement with the inner surface of the side wall 270A of the body 262. The upper surface of the bottom wall 280A includes a circular recess 280D for receipt of the lower large end of a flared, helical compression spring 282. The undersurface of the bottom wall 280A of the piston is planar.

A rolling diaphragm 284 (FIGS. 14 and 17) is mounted in the interior space 278 below the piston 280. The rolling diaphragm is a disk-shaped member formed of any suitable resilient material, e.g., silicone, nitrile, buna, or ethylene propylene diene monomer rubber (EPDM) and includes a beaded peripheral edge 284A which as best seen in FIGS. 18 and 19 is fixedly secured under the flange 266A sandwiched between the side wall 266 of the base 262 and the inner surface of the side wall 270A of the body 260. The rolling diaphragm 284 includes a portion that extends upward along the inner surface of the side wall 270A from whence it folds downward along the outer surface of the sidewall 280B of the piston, with the remainder of the diaphragm extending along the planar undersurface of the piston. The space between the conical recess 268 and the rolling diaphragm forms an expandable/contractible pressure chamber 268A which is in fluid communication with the passageway or conduit 264 and in which the inflation liquid 68 will be introduced.

The upper end of the compression spring 282 is open and receives the bottom end of an externally threaded stainless steel rod or shaft 286 with a washer 288 interposed therebetween to sandwich the spring between the thread rod or shaft and the piston 280. The threaded rod shaft 286 extends through a threaded bore 290 in the top wall of the body and is fixedly secured at its upper end to a low profile rotary knob 292 by means of a screw 294 and washer 296. The spring 282 is configured to provide a bias force onto the piston 280 to tend to push the piston and rolling diaphragm 284 towards the conical recess 268, thereby tending to contract the volume of the expandable/collapsible chamber 268a. The amount of force applied by the spring 282 is adjustable by the rotation of the knob 292 in either the clockwise or counterclockwise direction such that the pressure on the inflation liquid 68 in the chamber 268A will be at the desired operating level. Thus, by merely turning the knob in a desired rotational direction one can readily change the blood pressure that pressure regulator/accumulator 228 is set to regulate at.

In order to ensure that the spring remains in place and doesn't slip its lower end is located within the heretofore identified recess 280D of the piston.

As will be appreciated by those skilled in the art the existence of the piston transmits the force from the spring to the diaphragm, while ensuring uniform deformation of the diaphragm. In the exemplary embodiment shown, the spring is conical to reduce the solid height. This feature allows the pressure regulator/accumulator 228 to have the same fluid capacity as the regulators 28 and 128, but with a reduced size, in the interest of limiting visual and physical obstruction of the surgical field.

As best seen in FIG. 18 a small vent 298 is located within the top wall of the body 260 which prevents pressurization of the air opposing the rolling diaphragm.

As mentioned earlier the pressure regulator/accumulator 228 is configured to be mounted on the leg of a patient or some other structure by means of the strap mount 300 that is fixedly secured to the bottom of the base 262 of the pressure regulator/accumulator 228. The upper surface 300A (FIG. 18) of the strap mount 300 is planar, whereas its lower surface 300B is concave of the base 262. The strap mount 300 is a solid body formed of polycarbonate and includes four bores 302 extending through the body of the strap mount from the bottom surface 300B to the top surface 302 for receipt of the screws 274. The entryway to each bore is enlarged to receive the head of the screw. The base 260 includes a recess 260A (FIG. 16A) extending diametrically across the base. Thus, when the strap mount 300 is secured to the base 260, via the screws 274, a channel 304 (FIG. 19) is formed therebetween. A strap or some other band (not shown) can be extended through the channel and around the leg, e.g., thigh, of the patient or around some other structure to releasably mount the pressure regulator/accumulator 228 thereon and out of the surgical field, thereby reducing clutter in the surgical field. While the preferred embodiment of the invention 220 as just described makes use of a strap mount 300, other alternative variations of the mount are contemplated, e.g., mounts using sticker-type adhesives and Velcro straps for securing the pressure regulatory accumulator to the leg of the patient or to any desired structure.

The catheter of the system 220 is preferably packaged with a lubricant, e.g., silicone medical fluid, on the balloon for ease of insertion. That package includes a sleeve that is preassembled on the shaft of the catheter so that it can be slid over the balloon to compress the balloon and straighten the atraumatic tip before insertion. The lubricant could alternatively be on the interior of this sleeve.

The details of the operation of the system 220 will now be described. To that end, the pressure regulator/accumulator 228 is initially primed with the liquid 68 by means of the syringe 24 and without necessitating the use of a three way stop cock or any other similar component to switch the system to any of the three modes of operation. In particular, priming of the pressure regulator/accumulator is undertaken by orienting the catheter so that it is vertical with the balloon facing downward. The knob 292 of the pressure regulator/accumulator comes factory-set rotated to its maximum clockwise position. The outlet 66 of a filled syringe 24 is then introduced into the needleless injection site male luer lock 254 in the port 264A. The syringe's plunger 60 can then be depressed to inject a desired amount, e.g., 30 cc, of priming liquid 68 through the needleless injection site male luer lock 254 and into the passageway 264, from whence it flows to the balloon to fully inflate the balloon. The plunger of the syringe is then withdrawn to aspirate or pull air out of the system and to withdraw as much inflation liquid as possible from the balloon so that the balloon is fully deflated and therefore easily insertable into the femoral artery. That action leaves about 15 cc of residual liquid in the expandable/contractible chamber 268A and the catheter. The foregoing priming step is preferably done by inverting the pressure regulator/accumulator so that the conical recess 268 faces upward when the liquid is injected into the passageway 264. By so doing one improves the ability of the pressure regulator/accumulator 228 to be primed safely since any air within the chamber 268A in will rise to the top of the conical recess and be pulled out into the syringe 24 upon aspiration. The removal of all air from expandable/contractible chamber 286A is of considerable importance, because in the event of balloon rupture, any air inside the system 220 could enter the blood stream and cause an air embolism. It is advantageous to have the accumulator parts 260, 262, and 300 all made of polycarbonate or similarly transparent plastic, as that construction allows visual confirmation of air removal during priming. Having the base and strap mount transparent with an opaque housing is also acceptable.

Once the pressure regulator/accumulator 228 has been primed the syringe 24 can be removed, whereupon the needleless injection site male luer lock 254 will automatically seal the port 264A. The system 220 is now ready for use. To that end, the pressure regulator/accumulator can be mounted on the leg of the patient or some other structure using the strap mount 300, whereupon the pressure regulator/accumulator will be facing upward. The catheter 222, with its deflated balloon, can then be inserted into the patient's vasculature via the femoral artery.

Once the catheter 222 is in its operative position within the aorta, the syringe 24 can then be used to inject an additional desired volume, e.g., 30 cc, of inflation liquid 68 into the port 264A and through the luer lock 254. That injected liquid will flow out through the port 264B into the catheter 222, whereupon REBOA operation ensues. In particular, the volume of inflation liquid 68 injected into the port 264A will pass through the conduit 264 in pressure regulator/accumulator, out through the port 264B and into the inflation lumen 240 of the catheter from whence it will enter into the interior of the balloon to fill the balloon 236 to a level that occludes blood flow, yet at a pressure that will not burst or damage the aorta regardless of the size. This is due to the expandable volume of the chamber 268A. For example, if the diameter of the aorta is 12 mm injecting 30 cc of liquid 68 into the pressure regulator/accumulator will cause the balloon to fill and occlude the aorta and the pressure within the balloon will stay at a safe level, e.g., approximately 250 mm Hg. Without the expandable/contractible chamber 268A, injecting 30 cc could damage or burst the aorta. If the aorta is larger, e.g., 32 mm for example, the balloon will fill to a pressure of approximately 125 mm Hg which is adequate to occlude the aorta of a patient with low blood pressure, such as the patients that REBOA is used on. It should be noted that by design there is some give in the spring 282 so that the balloon will be prevented from becoming excessively pressurized.

Once the system is in the REBOA state the syringe 24 can then be removed from the port 264A, whereupon a needleless injection site male luer lock 254 will automatically seal itself. Since the conduit 264 is located in the bottom of the pressure regulator/accumulator its location reduces the chance that air should exit the pressure regulator/accumulator during use in the event of balloon rupture. Rather, any air will remain at the top of the pressure regulator/accumulator, and the inflation liquid (saline) would enter the bloodstream, to no ill effect.

In order to switch the system 220 to the pREBOA mode of operation, all that the user has to do is to rotate the knob 292 in the counterclockwise direction to a desired position to establish the pREBOA pressure, e.g., within the range of 60-80 mm Hg. In particular, the rotation of the knob in the counter-clockwise direction reduces the force applied by the spring to the piston and hence to the rolling diaphragm, whereupon the pressure chamber 268A will thus expand against the bias provided by the piston and spring so that the expanded pressure chamber will accept some of the sterile saline inflation liquid from the balloon. The higher pressure that previously existed in the aorta by virtue of the complete occlusion of the aorta by the balloon, will force some of the sterile saline inflation liquid within the balloon back through the lumen 240 and the communicating conduit 250A into the port 264B from whence it will flow through the opening 264C into the interior of the pressure chamber 268A. Accordingly, the balloon will deflate somewhat, i.e., be partially inflated. In short, the setting of the knob and compression spring will automatically control the amount of pressure applied to the balloon to the desired operating pressure to maintain brain perfusion, but enabling some blood to flow to the lower extremities. In order to precisely set the pREBOA pressure, a pressure monitoring device, such as a gauge or a vital signs monitor, can be attached to port 264A.

The switching of the system 220 between the REBOA mode and the pREBOA mode can be accomplished two ways. One is like that described above, wherein the threaded rod 286 is of such a length that the knob 292 can be turned to reduce the balloon pressure down to the desired regulation range. The regulation range would then be fully adjustable by the surgeon between the "full" occlusion pressure and a minimum pressure determined by the aorta size. In an extremely small aorta, it will be possible to achieve balloon pressures as low as 40 mm Hg, and larger aortas will permit even lower pressures. An alternative entails providing a pull tab (not shown) which will initially force the spring 282 down to give the high pressure required for REBOA. When it is desired to operate in pREBOA mode, the tab could be removed to reduce the compression on the spring and decrease the fluid pressure to a predetermined range. This configuration can be constructed with or without the threaded rod 286 and the knob 292. However, including the threaded rod and knob would allow fine tuning of the pressure as desired by the surgeon. Not having the threaded rod 286 would further reduce the bulk of the pressure regulator/accumulator.

As mentioned earlier the catheter includes a pressure monitoring lumen 240 which is in fluid communication via conduit 250B to either a vital sign monitor (VSM) 226 or a pressure gauge. The distal end of the pressure monitoring lumen 242 is in fluid communication with the open pressure monitoring port 258A at the distal end of the atraumatic tip 238 via the bridge tube 254. Accordingly, the pressure of the blood within the aorta above the balloon during REBOA or pREBOA can be monitored by the VSM or the pressure gauge.

As should be appreciated by those skilled in the art, the system 220 offers various advantages over the prior art, as well as advantages over the embodiments 20 and 120 of this invention. Insofar as the prior art is concerned, the following constitutes a method of deploying a REBOA as set forth in the instructions for use (IFU) of such catheters. In particular, such IFUs typically state that one has to estimate patient's aorta diameter and then use a reference chart to determine inflation volume. Needless to say such action is time consuming and prone to human error. In addition, the IFUs typically state that one should monitor the pressure on the syringe during inflation until it "feels" occluded. Such action is also prone to human error. Then, according to the IFU's the user is to look for an increase in blood pressure above the balloon to determine when occlusion (REBOA) is achieved. It should be noted that if the patient has too little blood left, the pressure may never rise, so this action could lead to over-inflation of the balloon. In contradistinction, the system 220 works such that once the catheter 222 is in the correct location, the surgeon simply fills the pressure regulator/accumulator 228 with a desired amount, e.g., 30 ccs of saline, no matter the patient, and the balloon 236 on the catheter will automatically inflate to the REBOA mode to thereby occlude the aorta. The surgeon is therefore free to do other tasks, and can be certain that the correct occlusion volume will be achieved in the balloon.

It should also be appreciated that since the inflation lumen 240 of the catheter only needs to be in communication with the interior of the balloon, the distal portion of the catheter can have a reduced diameter, compared to the catheters of systems 20 and 120, resulting in an asymmetric balloon, i.e., the distal neck or collar 256 is smaller than the proximal neck or collar 254 as mentioned above. While this feature reduces bulk for insertion, the bigger advantage of the asymmetric arrangement is in the removal of the catheter from the patient's body. In this regard, prior art REBOA catheters with symmetrical balloons have been known to get stuck within the patient such that emergency surgical intervention is required to get the catheter out of the patient's femoral artery. During insertion, the balloon wrapping/folding can be carefully controlled by the surgeon to prevent the body of the balloon from pulling down over the shaft of the catheter, but during removal the catheter must be pulled blindly as there is no way to visualize or manipulate the balloon inside the vasculature (although in some cases spinning the catheter does help with both insertion and removal). Having a smaller diameter neck or collar at the distal end of the balloon lessens the chances of the balloon becoming stuck during withdrawal. Moreover, the opening at the distal end of the inflation lumen 240 is located in the end of the catheter shaft 230, rather than within the body of the balloon (as is the case with the systems 20 and 120). This feature allows the catheter shaft to terminate before the balloon body, reducing the bulk of the balloon section, allowing a large balloon to be used without requiring a larger sheath.

Figure 21:
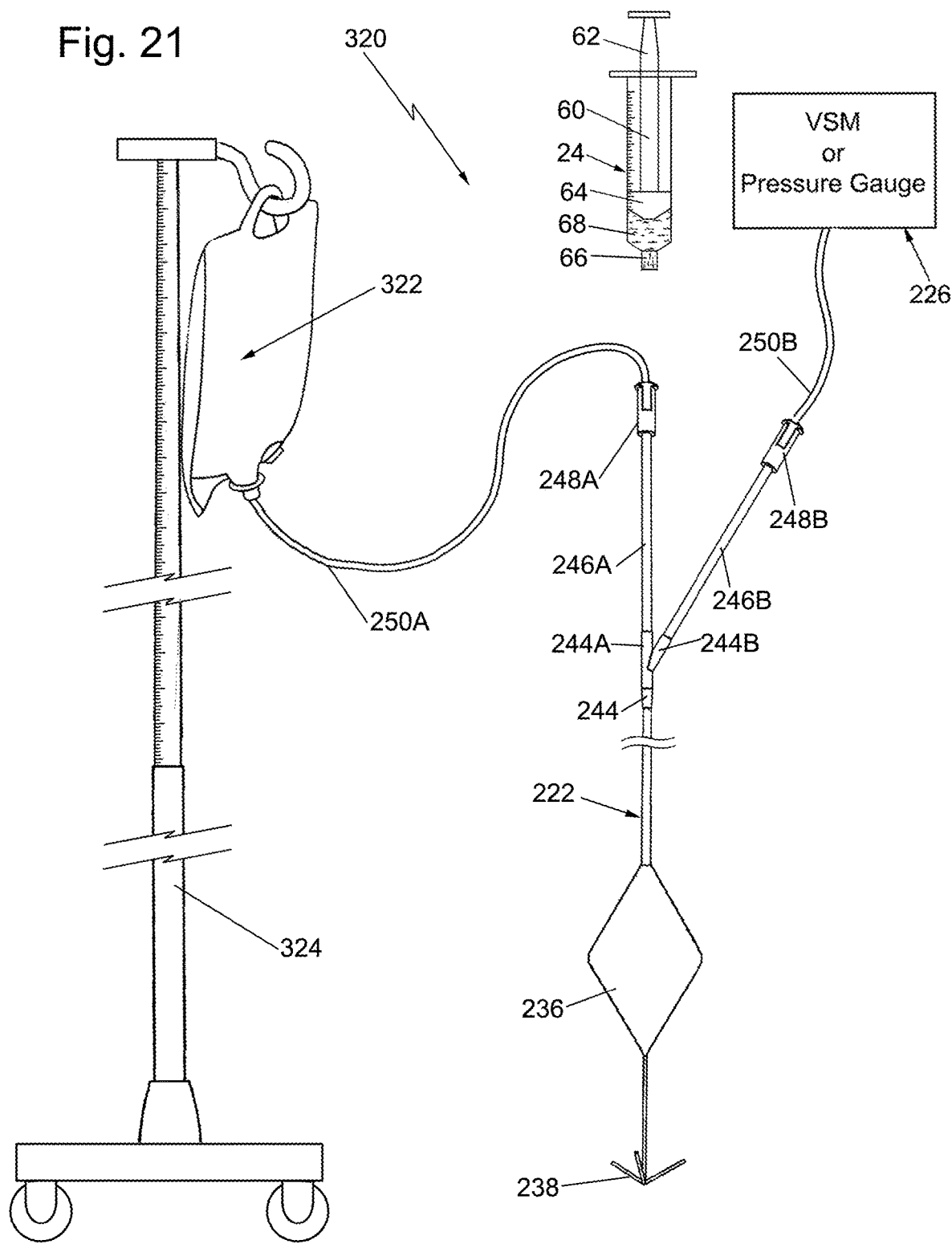
FIG. 21 is an isometric view, not to scale, of another exemplary system constructed in accordance with this invention for effecting the total and partial occlusion of a blood vessel, e.g., the aorta, of a living patient for various medical procedures, e.g., repair of an incompressible abdominal injury or wound.

In FIG. 21 there is shown another exemplary embodiment of a system 320 constructed in accordance with this invention. The system 320 is similar in many respects to the system 220, except that it does not include a pressure regulator accumulator 228 for effecting pREBOA operation. The system 320 is, however, configured for the three modes of operation of the system 220. In the interest of brevity those components of the system 320 which are identical in construction and operation with the like components of the apparatus 220 will be given the same reference numbers and their description and operation will not be reiterated. Thus, as can be seen the system 320 includes the syringe 24, the catheter 220 and the VSM or pressure gauge 226. It addition, the system includes a bag 322 of sterile inflation liquid (e.g., saline) 68 which is mounted on a stand or pole, e.g., a conventional adjustable height IV stand or pole, 324. The bag 322 serves as the means for receiving the inflation liquid 68 from the catheter 220 when the system 320 is in the pREBOA mode or state. In particular, the pReboa pressure could be controlled by attaching the bag of saline to the catheter balloon lumen and then changing the height of the bag relative to the balloon by adjusting the height of the pole 324 to change the pressure. Thus, pressure in the balloon will be the height of a column of water from the balloon to the top level of the saline 68 in the bag 322.

The system 320 can be primed by inserting the outlet port 66 of the syringe 24 into the female luer lock or connector 248A and injecting and aspirating the inflation liquid 68 into the balloon as described above. Once the catheter has been primed and collapsed, it is ready to be introduced into the aorta, as described above for REBOA operation. To that end, additional inflation liquid can be introduced into luer lock or connector 248A from whence it will flow into the balloon of the catheter to fill the catheter to the desired pressure to occlude the aorta. Alternatively, the inflation of the catheter to its REBOA state can be accomplished by raising the bag 322 to the appropriate height to produce the desired balloon inflation pressure and then connecting the tube 250A to the outlet of the bag, whereupon the inflation liquid 68 in the bag will flow into the connector 248A, from whence it will flow into the balloon to fill the balloon to that pressure, thereby occluding the aorta. When the system 320 is desired to be placed in the pREBOA mode, all that is necessary is to move the bag to the height necessary to establish the desired pressure for pREBOA.

Figure 22:
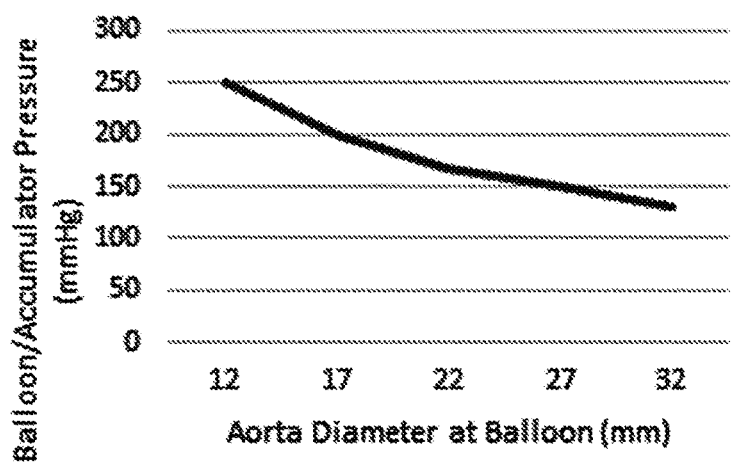
FIG. 22 is a graph which illustrates one aspect of the ability of a pressure regulator accumulator, like that of FIGS. 1 and 4.

Turning now to FIG. 22, there is shown a graph which represents the relationship between full REBOA pressure and the inner aorta diameter at the location of a spherical balloon, like that of systems 20 and 120, after injecting 30 cc into the catheter after priming. As can be seen, the endpoints of 12 mm and 32 mm represent the smallest and largest aortic diameters that one would expect to see in a patient at the location of the balloon. This is also the maximum pressure that would be delivered for a given size aorta. Thus, the graph of FIG. 22 illustrates the ability of the pressure regulator/accumulator of systems 20 and 120 to hold a relatively constant pressure over a wide range of aorta diameters. The pressure regulator/accumulator of system 220 will operate in a similar manner.

Figure 23:
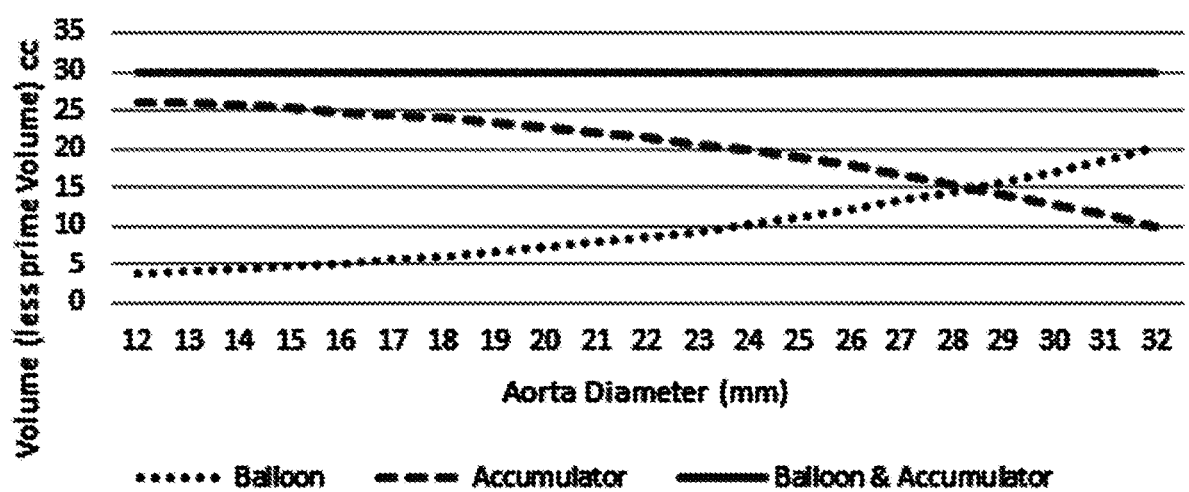
FIG. 23 is a graph which illustrates another aspect of the ability of a pressure regulator accumulator, like that of FIG. 8.

FIG. 23 is a graph showing the distribution of post-priming liquid 68 in the system 220 for various aorta diameters. With a smaller diameter aorta, balloon fill volume will be lower and therefore the pressure regulator accumulator volume will be higher and vice versa for a larger diameter aorta. Thus, the graph of FIG. 23 shows how the inflation liquid 68 gets distributed between the balloon and pressure regulator/accumulator across different aorta diameters in order to achieve the relatively constant pressure shown in the graph of FIG. 22.

In summary, all of the systems and methods of the subject invention provide definite advantages over the prior art by regulating the pressure superiorly to the balloon. With the subject invention when external pressure is applied the balloon will compress slightly, and the excess balloon volume will move back into the pressure regulator/accumulator, to maintain specified (desired) pressure. Similarly, if external pressure decreases, the pressure regulator/accumulator will automatically increase balloon volume to maintain a target pressure superior to the balloon. This allows clinicians to "set it and forget it" until the patient has been stabilized and limits the risk of vascular injury from over-pressurization above the occlusion site, while providing the benefits of REBOA and pREBOA. Moreover, the self-regulating operation of the systems of this invention work to maintain a minimum systolic blood pressure above the balloon while allowing as much blood to bypass the balloon as the patient is able to sustain. This allows volume loading and infusion to benefit the inferior portion of the body without the need to risk superior perfusion by manually deflating the balloon. By allowing partial blood flow, pREBOA can reduce the risk of ischemia below the balloon. pREBOA also offers the potential to extend acceptable occlusion times beyond the estimated 20-30 minutes in zone I and 60-90 minutes in zone III. Further yet, the likelihood of vascular injury from superior over-pressurization is decreased with pressure-regulated pREBOA because the balloon acts as a pressure relief valve. Finally, the controlled reperfusion made possible by the systems and methods of this invention should decrease the risk of reperfusion injury associated with deflation of the REBOA balloon.

Lastly, it should be pointed out that the systems and methods of this invention as described above are merely exemplary of many systems and methods contemplated by the subject invention. In this regard, while the discussion above has focused on complete and partial occlusion of the aorta to enable treatment of a traumatic injury, e.g. an incompressible abdominal injury, it should be clear that the subject invention is not limited to such use. Thus, the subject invention can be used in any blood vessel, arterial or venous, wherein it is desired to fully and partially occlude that vessel for any purpose. In fact, the subject invention is not limited to use in blood vessels, but can be used in any biological system of a patient to regulate circulation of any bodily fluid therein.

Without further elaboration the foregoing will so fully illustrate our invention that others may, by applying current or future knowledge, adopt the same for use under various conditions of service.

We claim:

1. A system for selectively effecting the total occlusion of the descending aorta of a living being during a REBOA procedure, the descending aorta including blood therein, said system also selectively effecting partial occlusion of the descending aorta when the system is in a pREBOA mode, said system being configured for manual control by a user and comprising:

a catheter having a distal end portion and at least one lumen extending through at least a portion of said catheter, said at least one lumen being configured to be selectively coupled a fluid reservoir to have a metered volume of a sterile liquid introduced into said at least one lumen whereupon said system is in a first mode of operation in said REBOA procedure;

a balloon located adjacent said distal end portion of said catheter, said balloon having a hollow interior coupled to said at least one lumen for selective receipt of said sterile liquid from said fluid reservoir to result in the full inflation of said balloon when said system is manually selected by the user to be in said first mode of operation, thereby completely occluding the descending aorta to preclude blood from flowing past said balloon when said system is in said first mode of operation; and a pressure regulator/accumulator coupled to said interior of said balloon via said at least one lumen to receive a portion of said sterile liquid from said balloon when said system is manually selected by the user to be in a second mode of operation during said pREBOA mode, whereupon said balloon is partially inflated to enable some blood in the descending aorta to flow past said balloon, said pressure regulator/accumulator automatically regulating the pressure within said partially inflated balloon to a desired pressure when said system is in said second mode of operation, said pressure regulator/accumulator comprising an expandable and collapsible chamber coupled to said catheter via said at least one lumen and configured to receive said portion of said sterile liquid from said balloon when said system is in said second mode of operation.

2. The system of claim 1, wherein said system is configurable so that said desired pressure is adjustable.

3. The system of claim 2, wherein said expandable and collapsible chamber is configured to receive a predetermined volume of said sterile liquid introduced therein to result in the application of a predetermined amount of bias force on said predetermined volume of said sterile liquid, whereupon said adjustable desired pressure is produced in said partially inflated balloon.

4. The system of claim 3, wherein said expandable and collapsible chamber comprises a resilient diaphragm.

5. The system of claim 4, wherein said pressure regulator/accumulator comprises a housing and wherein said resilient diaphragm is located within said housing.

6. The system of claim 1, wherein said balloon is configured to apply pressure in the range of approximately 40-250 mm Hg to the blood in the vessel.

7. The system of claim 1, wherein said at least one lumen comprises an inflation lumen and a pressure-monitoring lumen, and wherein said balloon includes a proximal end portion and a distal end portion, said hollow interior of said balloon being coupled to said inflation lumen at said distal end portion of said catheter, said pressure-monitoring lumen extending through said hollow interior of said balloon and exiting said balloon at said distal end portion of said balloon, said pressure monitoring lumen having a distal free end including a pressure-sensing opening.

8. The system of claim 7, wherein said pressure-monitoring lumen includes a proximal end portion configured to be coupled to a measuring instrument to provide an indication of the pressure within the blood vessel at said pressure-sensing opening.

9. The system of claim 8, wherein said distal free end comprises an atraumatic tip having a plurality of fingers located adjacent said pressure-sensing opening, said fingers projecting outwardly.

10. The system of claim 1, wherein said system is configured to be in a third mode of operation wherein the fluid reservoir and said pressure regulator/accumulator are in fluid communication with each other and isolated from said balloon.

* * * * *